(12) United States Patent
Kataoka et al.

(10) Patent No.: US 7,833,762 B2
(45) Date of Patent: Nov. 16, 2010

(54) METHOD FOR PRODUCING L-AMINO ACID

(75) Inventors: Saori Kataoka, Kawasaki (JP); Takuji Ueda, Kawasaki (JP); Yuji Joe, Kawasaki (JP); Chie Koseki, Kawasaki (JP)

(73) Assignee: Ajinomoto Co., Inc., Tokyo (JP)

( * ) Notice: Subject to any disclaimer, the term of this patent is extended or adjusted under 35 U.S.C. 154(b) by 0 days.

(21) Appl. No.: 12/241,233

(22) Filed: Sep. 30, 2008

(65) Prior Publication Data

US 2009/0087887 A1  Apr. 2, 2009

Related U.S. Application Data

(63) Continuation of application No. PCT/JP2007/057722, filed on Mar. 30, 2007.

(30) Foreign Application Priority Data

Mar. 30, 2006  (JP) ............... 2006-094784

(51) Int. Cl.
| | |
|---|---|
| C12P 13/04 | (2006.01) |
| C12P 13/08 | (2006.01) |
| C12N 9/00 | (2006.01) |
| C12N 1/20 | (2006.01) |
| C12N 15/00 | (2006.01) |
| C07H 21/04 | (2006.01) |

(52) U.S. Cl. ............... 435/115; 435/106; 435/183; 435/252.3; 435/320.1; 536/23.2

(58) Field of Classification Search ............... None
See application file for complete search history.

(56) References Cited

U.S. PATENT DOCUMENTS

| | | | |
|---|---|---|---|
| 5,661,012 A | 8/1997 | Sano et al. | |
| 5,827,698 A | 10/1998 | Kikuchi et al. | |
| 5,830,716 A | 11/1998 | Kojima et al. | |
| 5,932,453 A | 8/1999 | Kikuchi et al. | |
| 6,040,160 A | 3/2000 | Kojima et al. | |
| 7,300,776 B2 | 11/2007 | Ito et al. | |
| 7,306,933 B2 | 12/2007 | Dien et al. | |
| 2002/0025564 A1 | 2/2002 | Kobayashi et al. | |
| 2002/0160461 A1 | 10/2002 | Nakai et al. | |
| 2003/0017554 A1 | 1/2003 | Rieping et al. | |
| 2004/0229305 A1 | 11/2004 | Usuda et al. | |
| 2005/0059124 A1 | 3/2005 | Rieping | |
| 2005/0069994 A1 | 3/2005 | Ptitsyn et al. | |
| 2005/0170472 A1 | 8/2005 | Rieping | |
| 2005/0277179 A1 | 12/2005 | Takai et al. | |
| 2006/0019355 A1 | 1/2006 | Ueda et al. | |
| 2006/0088919 A1 | 4/2006 | Rybak et al. | |
| 2006/0160191 A1 | 7/2006 | Kataoka et al. | |
| 2007/0004014 A1 | 1/2007 | Tsuji et al. | |

FOREIGN PATENT DOCUMENTS

| | | |
|---|---|---|
| EP | 1510582 | 3/2005 |
| WO | WO03/008615 | 1/2003 |
| WO | WO 2006/038695 | 4/2006 |

OTHER PUBLICATIONS

Chica et al. Curr Opin Biotechnol. Aug. 2005;16(4):378-84.*
Sen et al. Appl Biochem Biotechnol. Dec. 2007;143(3):212-23.*
Imaizumi, A., et al., "Improved production of L-lysine by disruption of stationary phase-specific rmf gene in. Escherichia coli," J. Biotechnol. 2005;117:111-118.
International Search Report for PCT Patent App. No. PCT/JP2007/057722 (Nov. 6, 2007).
Kumari, S., et al., "Cloning, Characterization, and Functional Expression of acs, the Gene Which Encodes Acetyl Coenzyme A Synthetase in Escherichia coli," J. Bacteriol. 1995;177:10:2878-2886.
Lin, H., et al., "Acetyl-CoA synthetase overexpression in Escherichia coli demonstrates more efficient acetate assimilation and lower acetate accumulation: a potential tool in metabolic engineering," Appl. Microbiol. Biotechnol. 2006;71:870-874.
International Preliminary Report on Patentability for PCT Patent App. No. PCT/JP2007/057722 (Oct. 9, 2008).
U.S. Appl. No. 11/759,419, filed Jun. 7, 2007, Ueda et al.
U.S. Appl. No. 11/877,726, filed Oct. 24, 2007, Van Dien et al.
U.S. App. No. 12/056,390, filed Mar. 27, 2008, Ueda et al.
U.S. Appl. No. 12/056,414, filed Mar. 27, 2008, Ueda et al.
U.S. Appl. No. 12/212,743, filed Sep. 18, 2008, Rybak et al.
U.S. Appl. No. 10/149,450, filed Jun. 27, 2002, Nakanishi et al.

* cited by examiner

*Primary Examiner*—Christian L Fronda
(74) *Attorney, Agent, or Firm*—Shelly Guest Cermak; Cermak Nakajima LLP

(57) ABSTRACT

An L-amino acid is produced by culturing an L-amino acid-producing bacterium which belongs to the Enterobacteriaceae family and which has been modified so that the acetyl-CoA synthetase activity is increased.

1 Claim, No Drawings

METHOD FOR PRODUCING L-AMINO ACID

This application is a continuation under 35 U.S.C. §120 to PCT Patent Application No. PCT/JP2007/057722, filed on Mar. 30, 2007, which claims priority under 35 U.S.C. §119 to Japanese Patent Application No. 2006-094784, filed Mar. 30, 2006, both of which are incorporated by reference. The Sequence Listing in electronic format filed herewith is also hereby incorporated by reference in its entirety (File Name: US-337_Seq_List_Copy_1; File Size: 48 KB; Date Created: Sep. 30, 2008).

BACKGROUND OF THE INVENTION

1. Field of the Invention

The present invention relates to a method of producing an L-amino acid using a bacterium, and more particularly, to a method of producing an L-amino acid such as L-lysine, L-threonine, and L-glutamic acid. L-lysine and L-threonine are useful as additives in animal feeds, health food, amino acid infusions, and the like. L-glutamic acid is useful as a food seasoning.

2. Brief Description of the Related Art

L-amino acids have been industrially produced by fermentation using bacteria belonging to the genera *Brevibacterium, Corynebacterium, Escherichia*, or the like. Methods of producing L-lysine are described in EP 0643135 B, EP 0733712 B, EP 1477565 A, EP 0796912 A, EP 0837134 A, WO 01/53459, EP 1170376 A, and WO 2005/010175. In these methods, bacterial strains are used which are isolated from nature or artificial mutants thereof, as well as bacterial strains which have been modified to enhance the activity of an L-amino acid biosynthetic enzyme by recombinant DNA techniques.

Acetyl-CoA synthetase catalyzes a reaction to produce acetyl-CoA, pyrophosphate and AMP from acetic acid, coenzyme A and ATP, and is encoded by an acs gene (J Bacteriol. 1995 May; 177(10):2878-86.). However, there have been no reports that enhancing the activity of acetyl-CoA synthetase can be effective for L-amino acid production.

SUMMARY OF THE INVENTION

The present invention includes a bacterium which is capable of effectively producing an L-amino acid and a method of effectively producing an L-amino acid using the bacterium.

It has been found that production of an L-amino acid is improved by amplifying the acs gene encoding acetyl-CoA synthetase in an L-amino acid producing bacterium.

It is an aspect of the present invention to provide a method of producing an L-amino acid, comprising culturing a bacterium in a medium, and collecting the L-amino acid from the medium or bacterial cells, wherein said bacterium is an L-amino acid-producing bacterium belonging to the Enterobacteriaceae family which has been modified to enhance acetyl-CoA synthetase activity.

It is another aspect of the present invention to provide the method as described above, wherein the acetyl-CoA synthetase activity is enhanced by increasing the copy number of the acs gene which encodes the acetyl-CoA synthetase, or by modifying an expression regulatory sequence of said gene.

It is another aspect of the present invention to provide the method as described above, wherein said acs gene is selected from the group consisting of:

(a) a DNA comprising the nucleotide sequence of SEQ ID NO: 3; and (b) a DNA that hybridizes with a nucleotide sequence which is complementary to the nucleotide sequence of SEQ ID NO: 3, or with a probe that is prepared from the nucleotide sequence, under stringent conditions, and wherein said DNA encodes a protein with acetyl-CoA synthetase activity.

It is another aspect of the present invention to provide the method as described above, wherein the L-amino acid is selected from the group consisting of L-lysine, L-arginine, L-histidine, L-isoleucine, L-valine, L-leucine, L-threonine, L-phenylalanine, L-tyrosine, L-tryptophan, L-cysteine, L-glutamic acid, and combinations thereof.

It is another aspect of the present invention to provide the method as described above, wherein said bacterium belongs to the genus *Escherichia, Pantoea*, or *Enterobacter*.

DESCRIPTION OF THE PREFERRED EMBODIMENTS

Hereinafter, the present invention will be described in detail.

<1>Bacterium

The bacterium belongs to the Enterobacteriaceae family, and has an L-amino acid-producing ability, and is modified so that the activity of acetyl-CoA synthetase (ACS) is enhanced. Herein, the term "L-amino acid-producing ability" refers to the ability to produce and accumulate an L-amino acid in a medium at a collectable level when the bacterium is cultured in the medium. The bacterium may be able to produce a plurality of L-amino acids. The L-amino acid-producing ability may be native to the bacterium, or may be obtained by modifying the bacterium to impart the L-amino acid-producing ability by mutation or a recombinant DNA technique.

The kind of L-amino acid is not particularly limited, and examples thereof include the basic L-amino acids such as L-lysine, L-ornithine, L-arginine, L-histidine and L-citrulline; the aliphatic L-amino acids such as L-isoleucine, L-alanine, L-valine, L-leucine, and L-glycine; the hydroxy monoaminocarboxylic acids such as L-threonine and L-serine; the cyclic L-amino acids such as L-proline; the aromatic L-amino acids such as L-phenylalanine, L-tyrosine, and L-tryptophan; the sulfur-containing L-amino acids such as L-cysteine, L-cystine, and L-methionine; and the acidic L-amino acids such as L-glutamic acid, L-aspartic acid, L-glutamine, and L-asparagine. The bacterium may be able to produce two or more kinds of amino acids.

<1-1>Imparting L-amino Acid-Producing Ability

Hereinafter, methods of imparting the L-amino acid-producing ability will be described, as well as examples of the bacteria to which an L-amino acid-producing ability can be imparted. However, the bacterium is not limited thereto, as long as it has an L-amino acid-producing ability.

Bacteria belonging to the Enterobacteriaceae family, including those belonging to the genus *Escherichia* or *Pantoea*, can be used as the parent strain from which to derive the bacterium. Other examples of bacteria belonging to the Enterobacteriaceae family include γ-*Proteobacteria* such as *Enterobacter, Klebsiella, Serratia, Erwinia, Salmonella*, and *Morganella*.

*Escherichia* bacteria reported in Neidhardt et al. ((Backmann, B. J. 1996. Derivations and Genotypes of some mutant derivatives of *Escherichia coli* K-12, p. 2460-2488. Table 1. In F. D. Neidhardt (ed.), *Escherichia coli* and *Salmonella*

Cellular and Molecular Biology/Second Edition, American Society for Microbiology Press, Washington, D.C.), such as *Escherichia coli* can be utilized. Examples of a wild-type strain of *Escherichia coli* include the K-12 strain or derivatives thereof, *Escherichia coli* MG1655 strain (ATCC No. 47076), and W3110 strain (ATCC No. 27325). These strains are available from the American Type Culture Collection (ATCC) (Address: P.O. Box 1549, Manassas, Vir. 20108, 1, United States of America).

Examples of *Enterobacter* bacteria include *Enterobacter agglomerans* and *Enterobacter aerogenes*, and an example of *Pantoea* bacteria is *Pantoea ananatis*. Recently, *Enterobacter agglomerans* was reclassified in some cases as *Pantoea agglomerans, Pantoea ananatis, Pantoea stewartii*, or the like, based on an analysis of the nucleotide sequence of 16S rRNA. Therefore, bacteria may belong to either the genus *Enterobacter* or the genus *Pantoea*, as long as they are classified in the Enterobacteriaceae family. When *Pantoea ananatis* is bred using genetic engineering techniques, *Pantoea ananatis* AJ13355 strain (FERM BP-6614), AJ13356 strain (FERM BP-6615), AJ13601 strain (FERM BP-7207), derivatives thereof, and the like, may be used. These strains were identified and deposited as *Enterobacter agglomerans* when they were isolated, but as described above, these strains have been reclassified as *Pantoea ananatis* based on an analysis of the nucleotide sequence of 16S rRNA.

The L-amino acid-producing ability can be imparted to a parent strain as described above, as follows.

In order to impart the L-amino acid-producing ability, methods may be used which are used in conventional breeding of *Escherichia* bacteria or the like, such as by acquiring nutrient-auxotrophic mutant strains, analogue resistant strains, or metabolic regulation mutant strains, or by creating recombinant strains having enhanced expression of L-amino acid biosynthetic enzymes (Amino Acid Fermentation, Japan Scientific Societies Press, first edition publication: May 30, 1986, p. 77 to 100). Properties such as nutrient-auxotrophy, analogue-resistance, and metabolic regulation may be imparted alone or in combination with the methods for imparting the L-amino acid-producing ability. Furthermore, expression of one or more L-amino acid biosynthetic enzymes may be enhanced. Furthermore, imparting of such properties as nutrient-auxotrophy, analogue-resistance and metabolic regulation mutation may be combined with enhancing the expression of the L-amino acid biosynthetic enzymes.

Nutrient-auxotrophic mutant strains, L-amino acid-analogue resistant strains, and metabolic regulation mutant strains that have an L-amino acid-producing ability can be obtained as follows. A parent strain or a wild-type strain is subjected to a typical mutation treatment, such as irradiation with X-rays or ultraviolet rays, or by treating with a mutagen, including N-methyl-N'-nitro-N-nitrosoguanidine (NTG) and ethylmethanesulfonate (EMS), followed by selection of the strains that exhibit nutrient-auxotrophy, analogue-resistance, or a metabolic regulation mutation and have an L-amino acid-producing ability.

Gene recombination techniques include enhancing the expression of a gene encoding an enzyme involved in biosynthesis of a target L-amino acid and decreasing the expression of a gene encoding an enzyme involved in degradation of a target L-amino acid.

Hereinafter, a bacterium to which L-amino acid-producing ability is imparted will be exemplified, but bacteria to be used in the method are not limited to these examples.

L-threonine-Producing Bacteria

Examples of parent strains for deriving the L-threonine-producing bacteria include, but are not limited to, strains belonging to the genus *Escherichia*, such as *E. coli* TDH-6/pVIC40 (VKPM B-3996) (U.S. Pat. No. 5,175,107, U.S. Pat. No. 5,705,371), *E. coli* 472T23/pYN7 (ATCC 98081) (U.S. Pat. No. 5,631,157), *E. coli* NRRL-21593 (U.S. Pat. No. 5,939,307), *E. coli* FERM BP-3756 (U.S. Pat. No. 5,474,918), *E. coli* FERM BP-3519 and FERM BP-3520 (U.S. Pat. No. 5,376,538), *E. coli* MG442 (Gusyatiner et al., Genetika (in Russian), 14, 947-956 (1978)), *E. coli* VL643 and VL2055 (EP 1149911 A), and the like.

The TDH-6 strain is deficient in the thrC gene, as well as being sucrose-assimilative, and the ilvA gene has a leaky mutation. This strain also has a mutation in the rhtA gene, which imparts resistance to high concentrations of threonine or homoserine. The B-3996 strain contains pVIC40, which was obtained by inserting the thrA*BC operon which includes a mutant thrA gene into a RSF1010-derived vector. This mutant thrA gene encodes aspartokinase homoserine dehydrogenase I which is substantially desensitized to feedback inhibition by threonine. The B-3996 strain was deposited on Nov. 19, 1987 in the All-Union Scientific Center of Antibiotics (Nagatinskaya Street 3-A, 117105 Moscow, Russian Federation) under the accession number RIA 1867. This strain was also deposited in the Russian National Collection of Industrial Microorganisms (VKPM) (Russia, 117545 Moscow 1, Dorozhny proezd. 1) on Apr. 7, 1987 under the accession number B-3996.

*E. coli* VKPM B-5318 (EP 0593792B) may also be used to derive the L-threonine-producing bacteria. The B-5318 strain is prototrophic with regard to isoleucine, and a temperature-sensitive lambda-phage C1 repressor and PR promoter replaces the regulatory region of the threonine operon in plasmid pVIC40. The VKPM B-5318 strain was deposited in the Russian National Collection of Industrial Microorganisms (VKPM) on May 3, 1990 under accession number of VKPM B-5318.

Preferably, the bacterium is additionally modified to enhance expression of one or more of the following genes:

the mutant thrA gene which codes for aspartokinase homoserine dehydrogenase I resistant to feed back inhibition by threonine;

the thrB gene which codes for homoserine kinase;

the thrC gene which codes for threonine synthase;

the rhtA gene which codes for a putative transmembrane protein;

the asd gene which codes for aspartate-β-semialdehyde dehydrogenase; and the aspC gene which codes for aspartate aminotransferase (aspartate transaminase).

The sequence of the thrA gene of *Escherichia coli* which encodes aspartokinase homoserine dehydrogenase I has been elucidated (nucleotide positions 337 to 2799, GenBank accession NC_000913.2, gi: 49175990). The thrA gene is located between the thrL and thrB genes on the chromosome of *E. coli* K-12. The nucleotide sequence of the thrB gene of *Escherichia coli* which encodes homoserine kinase has been elucidated (nucleotide positions 2801 to 3733, GenBank accession NC_000913.2, gi: 49175990). The thrB gene is located between the thrA and thrC genes on the chromosome of *E. coli* K-12. The nucleotide sequence of the thrC gene of *Escherichia coli* which encodes threonine synthase has been elucidated (nucleotide positions 3734 to 5020, GenBank accession NC_000913.2, gi: 49175990). The thrC gene is located between the thrB gene and the yaaX open reading frame on the chromosome of *E. coli* K-12. All three genes function together as a single threonine operon. To enhance the expression of the threonine operon, the attenuator region which affects the transcription can be removed from the operon (WO2005/049808, WO2003/097839).

The mutated thrA gene which encodes feedback-resistant aspartokinase homoserine dehydrogenase I, as well as the thrB and thrC genes can be obtained as one operon from the well-known plasmid pVIC40. This plasmid is present in the threonine producing E. coli strain VKPM B-3996, and is described in detail in U.S. Pat. No. 5,705,371.

The rhtA gene is at 18 min on the E. coli chromosome close to the glnHPQ operon, which encodes components of the glutamine transport system. The rhtA gene is identical to ORF1 (ybiF gene, nucleotide positions 764 to 1651, GenBank accession number AAA218541, gi:440181) and is located between the pexB and ompX genes. The sequence expressing a protein encoded by the ORF1 has been designated the rhtA gene (rht: resistance to homoserine and threonine). Also, the rhtA23 mutation is an A-for-G substitution at position −1 with respect to the ATG start codon (ABSTRACTS of the 17th International Congress of Biochemistry and Molecular Biology in conjugation with Annual Meeting of the American Society for Biochemistry and Molecular Biology, San Francisco, Calif. Aug. 24-29, 1997, abstract No. 457, EP 1013765 A).

The nucleotide sequence of the asd gene of E. coli has already been elucidated (nucleotide positions 3572511 to 3571408, GenBank accession NC_000913.1, gi:16131307), and can be obtained by PCR (polymerase chain reaction; refer to White, T. J. et al., Trends Genet., 5, 185 (1989)) by utilizing primers based on the nucleotide sequence of the gene. The asd genes from other microorganisms can be obtained in a similar manner.

Also, the nucleotide sequence of the aspC gene of E. coli has already been elucidated (nucleotide positions 983742 to 984932, GenBank accession NC_000913.1, gi:16128895), and can be obtained by PCR. The aspC genes from other microorganisms can be obtained in a similar manner.

L-lysine-Producing Bacteria

Examples of L-lysine-producing bacteria belonging to the genus Escherichia include mutants having resistance to an L-lysine analogue. The L-lysine analogue inhibits growth of bacteria belonging to the genus Escherichia, but this inhibition is fully or partially desensitized when L-lysine is also present in the medium. Examples of the L-lysine analogue include, but are not limited to, oxalysine, lysine hydroxamate, S-(2-aminoethyl)-L-cysteine (AEC), γ-methyllysine, α-chlorocaprolactam and so forth. Mutants having resistance to these lysine analogues can be obtained by subjecting bacteria belonging to the genus Escherichia to a conventional artificial mutagenesis treatment. Specific examples of bacterial strains useful for producing L-lysine include Escherichia coli AJ11442 (FERM BP-1543, NRRL B-12185; see U.S. Pat. No. 4,346,170) and Escherichia coli VL611. In these microorganisms, feedback inhibition of aspartokinase by L-lysine is desensitized.

The strain WC196 may be used as an L-lysine producing bacterium of Escherichia coli. This bacterial strain was bred by conferring AEC resistance to the strain W3110, which was derived from Escherichia coli K-12. The resulting strain was designated Escherichia coli AJ13069 strain and was deposited at the National Institute of Bioscience and Human-Technology, Agency of Industrial Science and Technology (currently National Institute of Advanced Industrial Science and Technology, International Patent Organism Depositary, Tsukuba Central 6, 1-1, Higashi 1-Chome, Tsukuba-shi, Ibaraki-ken, 305-8566, Japan) on Dec. 6, 1994 and received an accession number of FERM P-14690. Then, it was converted to an international deposit under the provisions of the Budapest Treaty on Sep. 29, 1995, and received an accession number of FERM BP-5252 (U.S. Pat. No. 5,827,698).

Examples of parent strains for deriving L-lysine-producing bacteria also include strains in which expression of one or more genes encoding an L-lysine biosynthetic enzyme are enhanced. Examples of the enzymes involved in L-lysine biosynthesis include, but are not limited to, dihydrodipicolinate synthase (dapA), aspartokinase (lysC), dihydrodipicolinate reductase (dapB), diaminopimelate decarboxylase (lysA), diaminopimelate dehydrogenase (ddh) (U.S. Pat. No. 6,040,160), phosphoenolpyrvate carboxylase (ppc), aspartate semialdehyde dehydrogenease (asd), and aspartase (aspA) (EP 1253195 A). In addition, the parent strains may have increased expression of the gene involved in energy efficiency (cyo) (EP 1170376 A), the gene encoding nicotinamide nucleotide transhydrogenase (pntAB) (U.S. Pat. No. 5,830,716), the ybjE gene (WO2005/073390), the gdh gene (Gene 23:199-209(1983)), the arcA gene (EP 1382686A) or combinations thereof.

Examples of parent strains for deriving L-lysine-producing bacteria also include strains having decreased or eliminated activity of an enzyme that catalyzes a reaction for generating a compound other than L-lysine by branching off from the biosynthetic pathway of L-lysine. Examples of the enzymes that catalyze a reaction for generating a compound other than L-lysine by branching off from the biosynthetic pathway of L-lysine include homoserine dehydrogenase (WO 95/23864), lysine decarboxylase (U.S. Pat. No. 5,827,698), and the malic enzyme (WO2005/010175).

In Escherichia coli, lysine decarboxylases are encoded by a cadA gene (Genbank Accession No. NP_418555, SEQ ID NO: 5) and ldcC gene (Genbank Accession No. NP_414728, SEQ ID NO: 7) (WO 96/17930), so these genes may be disrupted to enhance L-lysine-producing ability. DNA molecules homologous to the cadA gene and ldcC gene may be used as long as they can cause homologous recombination with the cadA gene and ldcC gene on the chromosome of a host bacterium. For example, a DNA molecule homologous to the cadA gene may hybridize to a complementary strand of SEQ ID NO: 5 under stringent conditions, and a DNA molecule homologous to the ldcC gene may hybridize to a complementary strand of SEQ ID NO: 7 under stringent conditions.

L-cysteine-Producing Bacteria

Examples of parent strains for deriving L-cysteine-producing bacteria include, but are not limited to, strains belonging to the genus Escherichia, such as E. coli JM15 which has been transformed with different cysE alleles coding for feedback-resistant serine acetyltransferases (U.S. Pat. No. 6,218,168, Russian patent application 2003121601), E. coli W3110 which over-expresses genes which encode proteins suitable for secreting toxic substances (U.S. Pat. No. 5,972,663), E. coli strains with decreased cysteine desulfohydrase activity (JP11155571A2); E. coli W3110 with increased activity of a positive transcriptional regulator for the cysteine regulon encoded by the cysB gene (WO0127307A1), and the like.

L-leucine-Producing Bacteria

Examples of parent strains for deriving L-leucine-producing bacteria include, but are not limited to, strains belonging to the genus Escherichia, such as E. coli strains resistant to leucine (for example, the strain 57 (VKPM B-7386, U.S. Pat. No. 6,124,121)) or leucine analogs including β-2-thienylalanine, 3-hydroxyleucine, 4-azaleucine, 5,5,5-trifluoroleucine (JP 62-34397 B and JP 8-70879 A); E. coli strains obtained by the genetic engineering method described in WO96/06926; *E. coli* H-9068 (JP 8-70879 A), and the like.

The bacterium may be improved by enhancing the expression of one or more genes involved in L-leucine biosynthesis. Examples of these genes include those of the leuABCD operon, which preferably include a leuA gene which has been mutated so that it encodes isopropylmalate synthase which is resistant to feedback inhibition by L-leucine (U.S. Pat. No. 6,403,342). In addition, the bacterium may be improved by enhancing the expression of one or more genes coding for proteins which excrete L-amino acids from the bacterial cell. Examples of such genes include the b2682 and b2683 genes (ygaZH genes) (EP 1239041 A2).

L-histidine-Producing Bacteria

Examples of parent strains for deriving L-histidine-producing bacteria include, but are not limited to, strains belonging to the genus *Escherichia*, such as *E. coli* strain 24 (VKPM B-5945, RU2003677); *E. coli* strain 80 (VKPM B-7270, RU2119536); *E. coli* NRRL B-12116-B12121 (U.S. Pat. No. 4,388,405); *E. coli* H-9342 (FERM BP-6675) and H-9343 (FERM BP-6676) (U.S. Pat. No. 6,344,347); *E. coli* H-9341 (FERM BP-6674) (EP1085087); *E. coli* AI80/pFM201 (U.S. Pat. No. 6,258,554) and the like.

Examples of parent strains for deriving L-histidine-producing bacteria also include strains in which expression of one or more genes encoding an L-histidine biosynthetic enzyme are enhanced. Examples of these L-histidine-biosynthetic enzymes include ATP phosphoribosyltransferase (hisG), phosphoribosyl AMP cyclohydrolase (hisI), phosphoribosyl-ATP pyrophosphohydrolase (hisIE), phosphoribosylformimino-5-aminoimidazole carboxamide ribotide isomerase (hisA), amidotransferase (hisH), histidinol phosphate aminotransferase (hisC), histidinol phosphatase (hisB), histidinol dehydrogenase (hisD), and so forth.

It is known that the genes encoding the L-histidine biosynthetic enzyme (hisG, hisBHAFI) are inhibited by L-histidine, and therefore the L-histidine-producing ability can also be efficiently enhanced by introducing a mutation which induces resistance to the feedback inhibition into ATP phosphoribosyltransferase (hisG) (Russian Patent Nos. 2003677 and 2119536).

Specific examples of strains having an L-histidine-producing ability include *E. coli* FERM-P 5038 and 5048 which have been transformed with a vector carrying a DNA encoding an L-histidine-biosynthetic enzyme (JP 56-005099 A), *E. coli* strains transformed with rht, a gene for an amino acid-export (EP1016710A), *E. coli* 80 strain imparted with sulfaguanidine, DL-1,2,4-triazole-3-alanine, and streptomycin-resistance (VKPM B-7270, Russian Patent No. 2119536), and so forth.

L-glutamic Acid-Producing Bacteria

Examples of parent strains for deriving L-glutamic acid-producing bacteria include, but are not limited to, strains belonging to the genus *Escherichia*, such as *E. coli* VL334thrC$^+$ (EP 1172433). *E. coli* VL334 (VKPM B-1641) is auxotrophic for L-isoleucine and L-threonine and is mutated in the thrC and ilvA genes (U.S. Pat. No. 4,278,765). A wild-type allele of the thrC gene was transferred by general transduction using a bacteriophage P1 grown on the wild-type *E. coli* strain K12 (VKPM B-7). As a result, an L-isoleucine auxotrophic strain VL334thrC$^+$ (VKPM B-8961) was obtained.

Examples of parent strains for deriving the L-glutamic acid-producing bacteria include, but are not limited to, strains in which expression of one or more genes encoding an L-glutamic acid biosynthetic enzyme are enhanced. Examples of the enzymes involved in L-glutamic acid biosynthesis include glutamate dehydrogenase (gdhA), glutamine synthetase (glnA), glutamate synthetase (gltAB), isocitrate dehydrogenase (icdA), aconitate hydratase (acnA, acnB), citrate synthase (gltA), phosphoenolpyruvate carboxylase (ppc), pyruvate dehydrogenase (aceEF, 1pdA), pyruvate kinase (pykA, pykF), phosphoenolpyruvate synthase (ppsA), enolase (eno), phosphoglyceromutase (pgmA), phosphoglycerate kinase (pgk), glyceraldehyde-3-phophate dehydrogenase (gapA), triose phosphate isomerase (tpiA), fructose bisphosphate aldolase (fbp), phosphofructokinase (pfkA, pfkB), and glucose phosphate isomerase (pgi).

Examples of strains modified so that expression of the citrate synthetase gene, the phosphoenolpyruvate carboxylase gene, and/or the glutamate dehydrogenase gene is/are enhanced include those disclosed in EP1078989A, EP955368A, and EP952221A.

Examples of parent strains for deriving the L-glutamic acid-producing bacteria also include strains which have a decreased or eliminated activity of an enzyme that catalyzes synthesis of a compound other than L-glutamic acid, and branches off from the L-glutamic acid biosynthesis pathway. Examples of such enzymes include isocitrate lyase, α-ketoglutarate dehydrogenase, phosphotransacetylase, acetate kinase, acetohydroxy acid synthase, acetolactate synthase, formate acetyltransferase, lactate dehydrogenase, and glutamate decarboxylase. Bacteria belonging to the genus *Escherichia* deficient in the α-ketoglutarate dehydrogenase activity or having a reduced α-ketoglutarate dehydrogenase activity and methods for obtaining them are described in U.S. Pat. Nos. 5,378,616 and 5,573,945.

Specifically, these strains include the following:
*E. coli* W3110sucA:: Kmr
*E. coli* AJ12624 (FERM BP-3853)
*E. coli* AJ12628 (FERM BP-3854)
*E. coli* AJ12949 (FERM BP-4881)

*E. coli* W3110sucA::Kmr is obtained by disrupting the α-ketoglutarate dehydrogenase gene (hereinafter referred to as the "sucA gene") of *E. coli* W3110. This strain is completely deficient in α-ketoglutarate dehydrogenase.

Other examples of L-glutamic acid-producing bacterium include those which belong to the genus *Escherichia* and have resistance to an aspartic acid antimetabolite. These strains can also be deficient in α-ketoglutarate dehydrogenase activity and include, for example, *E. coli* AJ13199 (FERM BP-5807) (U.S. Pat. No. 5,908,768), FERM P-12379, which additionally has a low L-glutamic acid decomposing ability (U.S. Pat. No. 5,393,671); AJ13138 (FERM BP-5565) (U.S. Pat. No. 6,110,714), and the like.

Examples of L-glutamic acid-producing bacteria include mutant strains belonging to the genus *Pantoea* which are deficient in α-ketoglutarate dehydrogenase activity or have a decreased α-ketoglutarate dehydrogenase activity, and can be obtained as described above. Such strains include *Pantoea ananatis* AJ13356 (U.S. Pat. No. 6,331,419). *Pantoea ananatis* AJ13356 was deposited at the National Institute of Bioscience and Human-Technology, Agency of Industrial Science and Technology, Ministry of International Trade and Industry (currently, National Institute of Advanced Industrial Science and Technology, International Patent Organism Depositary, Central 6, 1-1, Higashi 1-Chome, Tsukuba-shi, Ibaraki-ken, 305-8566, Japan) on Feb. 19, 1998 under an accession number of FERM P-16645. It was then converted to an international deposit under the provisions of Budapest Treaty on Jan. 11, 1999 and received an accession number of FERM BP-6615. *Pantoea ananatis* AJ13356 is deficient in α-ketoglutarate dehydrogenase activity as a result of the disruption of the αKGDH-E1 subunit gene (sucA). The above strain was identified as *Enterobacter agglomerans* when it was isolated and deposited as the *Enterobacter agglomerans* AJ13356. However, it was recently re-classified as *Pantoea ananatis* on the basis of nucleotide sequencing of 16S rRNA and so forth. Although AJ13356 was deposited at the aforementioned depository as *Enterobacter agglomerans*, for the purposes of this specification, they are described as *Pantoea ananatis*.

L-phenylalanine-Producing Bacteria

Examples of parent strains for deriving L-phenylalanine-producing bacteria include, but are not limited to, strains belonging to the genus *Escherichia*, such as *E. coli* AJ12739 (tyrA::Tn10, tyrR) (VKPM B-8197); *E. coli* HW1089 (ATCC 55371) harboring the pheA34 gene (U.S. Pat. No. 5,354,672); *E. coli* MWEC101-b (KR8903681); *E. coli* NRRL B-12141, NRRL B-12145, NRRL B-12146 and NRRL B-12147 (U.S. Pat. No. 4,407,952). Also, as a parent strain, *E. coli* K-12 [W3110 (tyrA)/pPHAB (FERM BP-3566), *E. coli* K-12 [W3110 (tyrA)/pPHAD] (FERM BP-12659), *E. coli* K-12 [W3110 (tyrA)/pPHATerm] (FERM BP-12662) and *E. coli* K-12 [W3110 (tyrA)/pBR-aroG4, pACMAB] named as AJ 12604 (FERM BP-3579) may be used (EP 488424 B1). Furthermore, L-phenylalanine producing bacteria belonging to the genus *Escherichia* which have an enhanced activity of the protein encoded by the yedA gene or the yddG gene may also be used (U.S. patent applications 2003/0148473 A1 and 2003/0157667 A1).

L-tryptophan-Producing Bacteria

Examples of parent strains for deriving the L-tryptophan-producing bacteria include, but are not limited to, strains belonging to the genus *Escherichia*, such as *E. coli* JP4735/pMU3028 (DSM10122) and JP6015/pMU91 (DSM10123) deficient in the tryptophanyl-tRNA synthetase encoded by mutant trpS gene (U.S. Pat. No. 5,756,345); *E. coli* SV164 (pGH5) having a serA allele encoding phosphoglycerate dehydrogenase resistant to feedback inhibition by serine and a trpE allele encoding anthranilate synthase resistant to feedback inhibition by tryptophan (U.S. Pat. No. 6,180,373); *E. coli* AGX17 (pGX44) (NRRL B-12263) and AGX6(pGX50) aroP (NRRL B-12264) deficient in the enzyme tryptophanase (U.S. Pat. No. 4,371,614); *E. coli* AGX17/pGX50, pACKG4-pps in which a phosphoenolpyruvate-producing ability is enhanced (WO9708333, U.S. Pat. No. 6,319,696), and the like may be used. Furthermore, L-tryptophan producing bacteria belonging to the genus *Escherichia* which have an enhanced activity of the protein encoded by the yedA gene or the yddG gene may also be used (U.S. patent applications 2003/0148473 A1 and 2003/0157667 A1).

Examples of parent strains for deriving the L-tryptophan-producing bacteria also include strains in which one or more activities of the enzymes selected from anthranilate synthase (trpE), phosphoglycerate dehydrogenase (serA), and tryptophan synthase (trpAB) are enhanced. The anthranilate synthase and phosphoglycerate dehydrogenase are both subject to feedback inhibition by L-tryptophan and L-serine, so a mutation which results in desensitizing the feedback inhibition may be introduced into these enzymes. Specific examples of strains having such a mutation include an *E. coli* SV164 which harbors desensitized anthranilate synthase and a strain obtained by transforming the plasmid pGH5 into *E. coli* SV164 (WO 94/08031), which contains a serA gene which has been mutated so that it encodes feedback-desensitized phosphoglycerate dehydrogenase.

Examples of parent strains for deriving the L-tryptophan-producing bacteria also include strains transformed with the tryptophan operon which contains a gene encoding desensitized anthranilate synthase (JP 57-71397 A, JP 62-244382 A, U.S. Pat. No. 4,371,614). Moreover, L-tryptophan-producing ability may be imparted by enhancing expression of a gene which encodes tryptophan synthase, among tryptophan operons (trpBA). The tryptophan synthase consists of α and β subunits which are encoded by trpA and trpB, respectively. In addition, L-tryptophan-producing ability may be improved by enhancing expression of the isocitrate lyase-malate synthase operon (WO2005/103275).

L-proline-Producing Bacteria

Examples of parent strains for deriving L-proline-producing bacteria include, but are not limited to, strains belonging to the genus *Escherichia*, such as *E. coli* 702ilvA (VKPM B-8012) which is deficient in the ilvA gene and is able to produce L-proline (EP 1172433).

The bacterium may be improved by enhancing the expression of one or more genes involved in L-proline biosynthesis. Examples of preferred genes for L-proline producing bacteria include the proB gene coding for glutamate kinase which is desensitized to feedback inhibition by L-proline (DE Patent 3127361). In addition, the bacterium may be improved by enhancing the expression of one or more genes coding for proteins excreting L-amino acid from the bacterial cell. Such genes include the b2682 and b2683 genes (ygaZH genes) (EP1239041 A2).

Examples of bacteria belonging to the genus *Escherichia* which have an activity to produce L-proline include the following *E. coli* strains: NRRL B-12403 and NRRL B-12404 (GB Patent 2075056), VKPM B-8012 (Russian patent application 2000124295), plasmid mutants described in DE Patent 3127361, plasmid mutants described by Bloom F. R. et al (The 15th Miami winter symposium, 1983, p. 34), and the like.

L-arginine-Producing Bacteria

Examples of parent strains for deriving L-arginine-producing bacteria include, but are not limited to, strains belonging to the genus *Escherichia*, such as *E. coli* strain 237 (VKPM B-7925) (U.S. Patent Application 2002/058315 A1) and its derivative strains harboring mutant N-acetylglutamate synthase (Russian Patent Application No. 2001112869), *E. coli* strain 382 (VKPM B-7926) (EP1170358A1), an arginine-producing strain into which the argA gene encoding N-acetylglutamate synthetase is introduced (EP1170361A1), and the like.

Examples of parent strains for deriving L-arginine producing bacteria also include strains in which expression of one or more genes encoding an L-arginine biosynthetic enzyme are enhanced. Examples of the L-arginine biosynthetic enzymes include N-acetylglutamyl phosphate reductase (argC), ornithine acetyl transferase (argJ), N-acetylglutamate kinase (argB), acetylornithine transaminase (argD), ornithine carbamoyl transferase (argF), argininosuccinic acid synthetase (argG), argininosuccinic acid lyase (argH), and carbamoyl phosphate synthetase (carAB).

L-valine-Producing Bacteria

Example of parent strains for deriving L-valine-producing bacteria include, but are not limited to, strains which have been modified to overexpress the ilvGMEDA operon (U.S. Pat. No. 5,998,178). It is desirable to remove the region of the ilvGMEDA operon which is required for attenuation so that expression of the operon is not attenuated by the L-valine that is produced. Furthermore, the ilvA gene in the operon is desirably disrupted so that threonine deaminase activity is decreased. Examples of parent strains for deriving L-valine-producing bacteria also include mutants of amino-acyl t-RNA synthetase (U.S. Pat. No. 5,658,766). For example, *E. coli* VL1970, which has a mutation in the ileS gene encoding isoleucine tRNA synthetase, can be used. *E. coli* VL1970 has been deposited in the Russian National Collection of Industrial Microorganisms (VKPM) (Russia, 113545 Moscow, 1 Dorozhny Proezd.) on Jun. 24, 1988 under accession number VKPM B-4411.

Furthermore, mutants requiring lipoic acid for growth and/or lacking H⁺-ATPase can also be used (WO96/06926).

L-isoleucine-Producing Bacteria

Examples of parent strains for deriving L-isoleucine producing bacteria include, but are not limited to, mutants having resistance to 6-dimethylaminopurine (JP 5-304969 A), mutants having resistance to an isoleucine analogue such as thiaisoleucine and isoleucine hydroxamate, and mutants additionally having resistance to DL-ethionine and/or arginine hydroxamate (JP 5-130882 A). In addition, recombinant strains transformed with genes encoding proteins involved in L-isoleucine biosynthesis, such as threonine deaminase and acetohydroxate synthase, can also be used (JP 2-458 A, FR 0356739, and U.S. Pat. No. 5,998,178).

<1-2> Enhancement of ACS Activity

The bacterium can be obtained by modifying a bacterium having an L-amino acid-producing ability as described above so that the ACS activity is enhanced. However, the L-amino acid-producing ability may be imparted after the bacterium is modified so that the ACS activity is enhanced. As described below, the ACS activity can be enhanced by increasing the expression of a gene encoding a protein having ACS activity, which can be achieved by enhancing the expression of an endogenous gene by modifying an expression regulatory region such as a promoter, or enhancing expression of an exogenous gene by introducing a plasmid containing the gene, or the like. In addition, these methods may be combined.

The term "ACS activity" means an activity (EC 6.2.1.1) to catalyze a reaction to produce acetyl-CoA, pyrophosphate, and AMP from acetic acid, coenzyme A (CoA) and ATP.

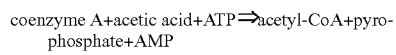
coenzyme A+acetic acid+ATP⇒acetyl-CoA+pyrophosphate+AMP

It has also been reported that ACS catalyzes a reaction to produce propionyl-CoA from propionic acid (Eur J Biochem 2002; 269(24); 6184-94), and it has also been reported that ACS could function as a 4-coumarate CoA lygase (Genome Biol 4(9); R54).

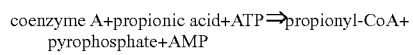
coenzyme A+propionic acid+ATP⇒propionyl-CoA+ pyrophosphate+AMP

coenzyme A+4-coumarate+ATP⇒coumaroyl-CoA+ pyrophosphate+AMP

The enhancement of ACS activity can be confirmed by measuring the amount of acetohydroxamic acid which is obtained by conversion of acetyl-CoA that is generated in vitro by the above-mentioned reaction (Meth. Enzymol. 1, 585-591). The phrase "modifying so that the ACS activity is enhanced" includes when the number of ACS molecules per cell increases and when the ACS activity per molecule is improved as compared to a wild-type strain or unmodified strain. The ACS activity is improved not less than 150% per cell, preferably not less than 200% per cell, more preferably not less than 300% per cell as compared to a wild-type strain or an unmodified strain. Examples of a wild-type strain belonging to the Enterobacteriaceae family which can be used as a control include *Escherichia coli* MG1655 strain (ATCC No. 47076), W3110 strain (ATCC No. 27325), and *Pantoea ananatis* AJ13335 strain (FERM BP-6615).

The ACS activity can be enhanced by increasing the expression of a gene encoding a protein having ACS activity (acs gene). The increased expression as compared to a wild-type or unmodified strain can be confirmed by comparing the mRNA level of the acs gene to that of a wild-type or unmodified strain. Methods for confirming the expression of a gene include Northern hybridization and RT-PCR (Molecular cloning (Cold spring Harbor Laboratory Press, Cold spring Harbor (USA), 2001)). The expression may be any level as long as it is increased as compared to a wild-type or unmodified strain, and for example, the expression is preferably increased not less than 1.5-fold, more preferably not less than 2-fold, and further more preferably not less than 3-fold as compared to a wild-type or unmodified strain. Meanwhile, enhancing the expression of the acs gene may also be confirmed by an increase in the level of the corresponding protein as compared to a wild-type or unmodified strain, and the protein level may be detected, for example, by Western blotting using an antibody (Molecular Cloning (Cold Spring Harbor Laboratory Press, Cold Spring Harbor (USA), 2001)).

Examples of the acs gene include the acs gene from *Escherichia coli*. Examples of acs gene of *Escherichia coli* include the acs gene of SEQ ID NO: 3 (a complementary strand of nucleotide numbers 4283436 . . . 4285394 of GenBank Accession No. NC_000913).

Examples of acs genes from other sources include the acs gene of *Yersinia pestis* (a complementary strand of nucleotide numbers 577565 . . . 579529 of GenBank Accession No. NC_004088), the acs gene of *Salmonella typhi* (a complementary strand of nucleotide numbers 120832 . . . 122790 of GenBank Accession No. AL627282), the acs gene of *Vibrio cholerae* (a complementary strand of nucleotide numbers 305121 . . . 307121 of GenBank Accession No. NC_002505) and the acs gene of *Salmonella typhimuriumi* (a complementary strand of nucleotide numbers 4513714 . . . 4515672 of GenBank Accession No. NC_003197).

In addition, the homologues of the acs gene can be obtained by cloning, based on homologies to the above-listed genes, from γ-proteobacterium that belongs to the genus *Escherichia, Enterobacter, Klebsiella, Serratia, Erwinia, Yersinia*, or the like; a coryneform bacterium such as *Corynebacterium glutamicum*, or *Brevibacterium lactofermentum*, a *Pseudomonas* bacterium such as *Pseudomonas aeruginosa*; a *Mycobacterium* bacterium such as *Mycobacterium tuberculosis*; or the like. The homologues may be amplified by PCR using, for example, synthetic oligonucleotides shown in SEQ ID NOS: 1 and 2.

The homologies between the amino acid sequences and nucleotide sequences can be determined by using the algorithm BLAST developed by Karlin and Altschul (Pro. Natl. Acad. Sci. USA, 90, 5873 (1993)) or the algorithm FASTA developed by Pearson (Methods Enzymol., 183, 63 (1990)). Based on the algorithm BLAST, programs called BLASTN and BLASTX have been developed (http://www.ncbi.nlm.nih.gov).

The phrase "homologue of the acs gene" includes a gene derived from other bacteria and a naturally or artificially mutated gene, which has high structural similarity to the above-mentioned acs gene and encodes a protein having ACS. The "homologues of the acs gene" include genes which encode a protein which has homology of at least 80%, preferably at least 90%, more preferably 95%, particularly preferably at least 98% to the entire sequence of SEQ ID NO: 4, and has ACS activity. ACS activity can be confirmed by expressing the gene in a host cell and measuring the ACS activity.

Meanwhile, the acs gene is not limited to a wild-type gene and may be a mutant or artificially modified gene that encodes a protein having the amino acid sequence of SEQ ID NO: 4, but which may include substitution, deletion, insertion, or addition of one or several amino acids at one or a plurality of positions as long as the ACS activity is maintained. Although it depends on the positions in the ternary structure and types of amino acid residues in the proteins, the term "one or several" specifically means 1 to 20, preferably 1 to 10, and more preferably 1 to 5. The above-mentioned substitution is preferably a conservative substitution, and examples of conservative substitutions include substitution between aromatic amino acids such as a substitution among Phe, Trp, and Tyr; substitution between hydrophobic amino acids such as a substitution among Leu, Ile, and Val; substitution between polar amino acids such as a substitution between Gln and Asn; substitution between basic amino acids such as a substitution among Lys, Arg, and His; substitution between acidic amino acids such as a substitution between Asp and Glu; substitution between amino acids having a hydroxyl group such as a substitution between Ser and Thr. Specific examples of a conservative substitution include substitution of Ser or Thr for Ala; substitution of Gln, His, or Lys for Arg; substitution of Glu, Gln, Lys, His, or Asp for Asn; substitution of Asn, Glu, or Gln for Asp; substitution of Ser or Ala for Cys; substitution of Asn, Glu, Lys, His, Asp, or Arg for Gln; substitution of Gly, Asn, Gln, Lys, or Asp for Glu; substitution of Pro for Gly; substitution of Asn, Lys, Gln, Arg, or Tyr for His; substitution of Leu, Met, Val, or Phe for Ile; substitution of Ile, Met, Val, or Phe for Leu; substitution of Asn, Glu, Gln, His, or Arg for Lys; substitution of Ile, Leu, Val, or Phe for Met; substitution of Trp, Tyr, Met, Ile, or Leu for Phe; substitution of Thr or Ala for Ser; substitution of Ser or Ala for Thr; substitution of Phe or Tyr for Trp; substitution of His, Phe, or Trp for Tyr; and substitution of Met, Ile, or Leu for Val. Meanwhile, the above-mentioned amino acid substitution, deletion, insertion, addition, or inversion may be a naturally occurring mutation (mutant or variant) due to an individual difference, a difference of types, or the like among the bacteria harboring the acs gene.

Meanwhile, the acs gene may be a DNA which hybridizes with a nucleotide sequence complementary to SEQ ID NO: 3, or a probe that can be prepared from the sequence under stringent conditions, as long as the gene encodes a protein having the ACS activity. The term "stringent conditions" refers to conditions where a so-called specific hybrid is formed and non-specific hybrid is not formed. It is difficult to clearly define the conditions by a numerical value, and examples include conditions where DNAs having high homology, for example, DNAs having homology of at least 80%, preferably at least 90%, more preferably at least 95%, or particularly preferably at least 98% hybridize with each other and DNAs having homology of less than 80% do not hybridize with each other; and specific examples thereof include washing in general Southern hybridization, i.e., washing at the salt concentration of 1×SSC, 0.1% SDS, preferably 0.1× SSC, 0.1% SDS, at 60° C., preferably at 68° C., once, preferably twice or three times.

Expression of the above-mentioned acs gene can be increased by, for example, increasing the copy number of the gene in a cell using a gene recombination technique. For example, a DNA fragment containing the gene is ligated to a vector that functions in the host bacterium, preferably a multi-copy vector, to thereby prepare a recombinant DNA, and the recombinant DNA is used to transform the host bacterium.

When using the acs gene of *Escherichia coli*, the acs gene can be obtained by PCR (polymerase chain reaction; White, T. J. et al., Trends Genet. 5, 185 (1989)) using primers based on the nucleotide sequence of SEQ ID NO: 3, for example, primers of SEQ ID NOS: 1 and 2 and a chromosomal DNA of *Escherichia coli* as the template. The acs gene from a different bacterium can also be obtained by PCR from the the chromosomal DNA or genomic DNA library of the chosen bacterium using, as primers, oligonucleotides prepared based on the known sequence of the acs gene of the chosen bacterium or of the acs gene of another kind of bacterium, or the amino acid sequence of the ACS protein. The acs gene may also be obtains from a different bacterium by hybridization using an oligonucleotide prepared based on the sequence as a probe. A chromosomal DNA can be prepared from a bacterium that serves as a DNA donor by the method of Saito and Miura (Biochem. Biophys. Acta, 72, 619 (1963), Experiment Manual for Biotechnology, edited by The Society for Biotechnology, Japan, p 97-98, Baifukan Co., Ltd., 1992) or the like.

Then, a recombinant DNA is prepared by ligating the acs gene which has been amplified by PCR to a vector DNA which is capable of functioning in the host bacterium. Examples of a vector capable of functioning in the host bacterium include vectors which are able to autonomously replicate in the host bacterium.

Examples of a vector which is autonomously replicable in *Escherichia coli* include pUC19, pUC18, pHSG299, pHSG399, pHSG398, pACYC184, (pHSG and pACYC are available from Takara Bio Inc.), RSF1010 (Gene vol. 75(2), p 271-288, 1989), pBR322, pMW219, pMW119 (pMW is available form Nippon Gene Co., Ltd.), pSTV28, and pSTV29 (Takara Bio Inc.). A phage DNA vector can also be used.

To ligate the gene to the above-mentioned vector, the vector is digested with a restriction enzyme corresponding to a recognition site in the terminus of a DNA fragment containing the acs gene. Ligation is generally performed using a ligase such as T4 DNA ligase. Methods of digesting and ligating DNA, preparation of a chromosomal DNA, preparation of a plasmid DNA, transformation, PCR, design of oligonucleotides to be used as primers are well known to the person skilled in the art. These methods are described in Sambrook, J., Fritsch, E. F., and Maniatis, T., "Molecular Cloning A Laboratory Manual, Second Edition", Cold Sprig Harbor Laboratory Press, (1989), and the like.

The thus-prepared recombinant DNA is introduced into a bacterium by a conventional transformation method, such as electroporation (Canadian Journal of Microbiology, 43. 197 (1997)). It is also possible to increase the DNA permeability by treating the recipient cells with calcium chloride, which has been reported for *Escherichia coli* K-12 (Mandel, M. and Higa, A., J. Mol. Biol., 53, 159 (1970), and introduce a DNA into a competent cell at the proliferation stage, which has been reported with *Bacillus subtilis* (Duncan, C. H., Wilson, G. A and Young, F. E, Gene, 1, 153 (1977)).

The copy number of the acs gene can also be increased by introducing multiple copies of the gene into the chromosomal DNA of the host bacterium. Introducing multiple copies of the gene into the chromosomal DNA of the host bacterium can be attained by homologous recombination using a target sequence present on the chromosomal DNA in multiple copies. This may be a repetitive DNA or an inverted repeat present on the end of a transposing element. Alternatively, as disclosed in JP 2-109985 A, multiple copies of the acs gene can be introduced into the chromosomal DNA by inserting the gene into a transposon, and transferring it so that multiple copies of the gene are integrated into the chromosomal DNA. Integration of the gene into the chromosome can be confirmed by Southern hybridization using a portion of the gene as a probe.

Furthermore, expression of the acs gene may be enhanced by, as described in WO 00/18935, WO98/04715, substituting an expression regulatory sequence such as the native promoter with a stronger promoter, whether the gene is present on the chromosome or a plasmid, amplifying a regulatory element that is able to increase expression of the gene, or deleting or attenuating a regulatory element that decreases expression of the acs gene. Examples of known strong promoters include the lac promoter, trp promoter, trc promoter, tac promoter, lambda phage PR promoter, PL promoter, and tet promoter.

A method to evaluate the strength of a promoter and examples of strong promoters are described in Goldstein et al. (Prokaryotic promoters in biotechnology. Biotechnol. Annu. Rev., 1995, 1, 105-128) or the like. In addition, it is known that a spacer sequence between the ribosome binding site (RBS) and the translation initiation codon, especially, several nucleotides just upstream of the initiation codon, has a great influence on translation efficiency. Therefore, this sequence may be modified.

In addition, to enhance the activity of a protein encoded by the acsA gene, a mutation that increases the ACS activity may be introduced into the gene. Examples of such a mutation include a mutation in the promoter sequence to increase the transcription level of acs gene, and a mutation in the coding region to increase the specific activities of the ACS protein.
[0046]
<2> Method of Producing L-amino Acid The method of producing an L-amino acid includes culturing the bacterium in a medium to produce and accumulate an L-amino acid in the medium or bacterial cells, and collecting the L-amino acid from the medium or the bacterial cells.

Conventional media which are typically used in bacterial fermentative production of an L-amino acid can be used. That is, a general medium containing a carbon source, nitrogen source, inorganic ion, and if necessary, other organic components can be used. Examples of the carbon source include sugars such as glucose, sucrose, lactose, galactose, fructose and a starch hydrolysate; alcohols such as glycerol and sorbitol; and organic acids such as fumaric acid, citric acid and succinic acid. Examples of the nitrogen source include inorganic ammonium salts such as ammonium sulfate, ammonium chloride and ammonium phosphate; an organic nitrogen such as a soybean hydrolysate; ammonia gas; and aqueous ammonia. As organic trace nutrients, auxotrophic substances such as vitamin B1 and L-homoserine, yeast extract, and the like are preferably contained in the medium in appropriate amounts. Besides such substances, if necessary, potassium phosphate, magnesium sulfate, iron ion, manganese ion, or the like may be added in small amounts. The chosen medium may be a natural medium or a synthetic medium as long as it contains a carbon source, nitrogen source, inorganic ion, and if necessary, other organic trace nutrients.

The culture is preferably performed under aerobic conditions for 1 to 7 days at a temperature of 24° C. to 37° C. and a pH of 5 to 9. The pH can be adjusted with an inorganic or organic acidic or alkaline substance, ammonia gas or the like. The L-amino acid can be collected from the fermentation liquid by a conventional method such as ion-exchange resin, precipitation, and other known methods. When the L-amino acid accumulates in the bacterial cells, the L-amino acid can be collected, for example, by disrupting the bacterial cells by ultrasonication or the like to release the L-amino acid into the supernatant fraction, and then the bacterial cells are removed by centrifugation, followed by subjecting the resulting supernatant fraction to an ion-exchange resin or the like.

When producing a basic L-amino acid, fermentation may be performed while controlling the pH of the medium during culture to 6.5-9.0 and controlling the pH of the medium after completion of the culture to 7.2-9.0, as well as controlling the pressure in the fermentation tank during fermentation so that it is positive. Alternatively, carbon dioxide or a mixed gas containing carbon dioxide may be added to the medium so that a bicarbonate ion and/or carbonate ion are present in an amount of at least 2 g/L in the culture medium during the culture period. These ions function as counter ions against the cation of the basic L-amino acids, and the target basic L-amino acid can be collected (EP1182261, WO2006/038695).

EXAMPLES

Hereinafter, the present invention will be described in more detail by referring to the following non-limiting examples.

Example 1

<1> Construction of a Plasmid for Amplifying the acs Gene

To evaluate the effect of amplification of the acs gene on production of L-lysine, a plasmid vector for amplifying the acs gene was constructed. The entire chromosomal nucleotide sequence of *Escherichia coli* (*Escherichia coli* K-12 strain) has been disclosed (Science, 277, 1453-1474 (1997)). Based on the nucleotide sequence of the acs gene that is disclosed in this document, the oligonucleotide of SEQ ID NO: 2 that contains a SalI site attached to the sequence complementary to nucleotides 4285765 to 4285784 of GenBank ACCESSION No. NC_000913 was used as the 5'-primer, and the oligonucleotide of SEQ ID NO: 1 that contains a BamHI site attached to the sequence of 4283415 to 4283435 of No. NC_000913 was used as 3'-primer. These primers were used to perform PCR using the chromosomal DNA of *Escherichia coli* MG1655 strain as a template.

The amplified acs gene was purified and digested with SalI and BamHI, and then ligated to SalI and BamHI-digested vector, pMW119 (Takara Bio), to obtain a plasmid for amplifying the acs gene (pMWacs).

Example 2

Construction of a Strain with Disrupted Lysine Decarboxylase-Encoding Genes (cadA and 1dcC)

A strain which produces no lysine decarboxylase was constructed. The lysine decarboxylases are encoded by the cadA gene (Genbank Accession No. NP-418555, SEQ ID NO: 5) and the 1dcC gene (Genbank Accession No. NP-414728, SEQ ID NO: 7) (WO 96/17930). *Escherichia coli* WC196 (FERM BP-5252) was used as a parent strain (WO96/17930).

The cadA gene and the 1dcC gene were disrupted by the method developed by Datsenko and Wanner, which is called "Red-driven integration" (Proc. Natl. Acad. Sci. USA, 2000, vol. 97, No. 12, p 6640-6645), and by an excision system derived from λ phage (J. Bacteriol. 2002 September; 184(18): 5200-3. Interactions between integrase and excisionase in the phage lambda excisive nucleoprotein complex. Cho E H, Gumport R I, Gardner J F.). "Red-driven integration" makes it possible to construct a gene-disrupted strain in one step by employing a PCR product obtained by using as primers synthetic oligonucleotides designed to have a part of the targeted gene on the 5'-ends and a part of an antibiotic-resistance gene on the 3'-ends. Combining with the λ phage-derived excision system permits the removal of the antibiotic-resistance gene that has been incorporated into the gene-disrupted strain (WO2005/010175).

(2-1) Disruption of the cadA Gene

The pMW118-attL-Cm-attR plasmid (WO2005/010175) was used as a template for PCR. pMW118-attL-Cm-attR was obtained by inserting the attL and attR genes, which are attachment sites for λ phage, and the cat gene, which is an antibiotic resistance gene, into pMW118 (Takara Bio Inc.) The genes are arranged in the following order: attL-cat-attR.

PCR was performed using, as primers, the synthetic oligonucleotides shown in SEQ ID NOS: 9 and 10, which have sequences corresponding to attL and attR on the 3'-ends and a sequence corresponding to a part of the targeted cadA gene on the 5'-ends.

The amplified PCR product was purified on an agarose gel and introduced into the *Escherichia coli* WC196 strain by electroporation. This strain harbors pKD46 which has temperature-sensitive replicability. pKD46 (Proc. Natl. Acad. Sci. USA, 2000, vol. 97, No. 12, p 6640-6645) contains a DNA fragment of 2,154 nucleotides derived from λ phage which contains the Red recombinase-encoding genes (γ, β, and exo genes) of the λ Red homologous recombination system, which is controlled by an arabinose-inducible ParaB promoter (GenBank/EMBL Accession No. J02459, nucleotide numbers 31088 to 33241). pKD46 is necessary to integrate the PCR product into the chromosome of the WC196 strain.

Competent cells for electroporation were prepared as follows. That is, cells of the *Escherichia coli* WC196 strain with pKD46 were cultured overnight at 30° C. in LB medium containing 100 mg/L ampicillin, and then diluted 100-fold with 5 mL of SOB medium (Molecular Cloning: Laboratory manual, 2nd edition, Sambrook, J. et al., Cold Spring Harbor Laboratory Press (1989)) containing ampicillin (20 mg/L) and L-arabinose (1 mM). The diluted cells were grown with aeration at 30° C. until the OD600 reached about 0.6, and then concentrated 100-fold and washed three times with 10% glycerol so that the cells were available for electroporation. The electroporation was performed with 70 μL of the competent cells and about 100 mg of the PCR product. After the electroporation, 1 mL of SOC medium (Molecular Cloning: Laboratory manual, 2nd edition, Sambrook, J. et al., Cold Spring Harbor Laboratory Press (1989)) was added to the cells, and cells were cultured at 37° C. for 2.5 hours, and then subjected to plate culture onto L-agar medium containing Cm (chloramphenicol) (25 mg/L), to thereby select Cm-resistant recombinant strains. Subsequently, to remove the plasmid pKD46, the cells were subcultured twice at 42° C. on L-agar medium containing Cm, and ampicillin resistance of the resultant colonies were examined, to thereby yield ampicillin-sensitive strains in which the pKD46 was cured.

Deletion of the cadA gene in the mutant strain, which had been identified by the chloramphenicol-resistance gene, was confirmed by PCR. The cadA-disrupted strain was named WC196ΔcadA::att-cat.

Subsequently, the helper plasmid pMW-intxis-ts (WO2005/010175) was used to remove the att-cat gene which had been introduced into the cadA gene. The plasmid pMW-intxis-ts carries a gene encoding the integrase (Int) of λ phage, and the gene encoding excisionase (Xis), and has temperature-sensitive replicability.

Competent cells of the WC196ΔcadA::att-cat strain were prepared by a conventional method, and were then transformed with the helper plasmid pMW-intxis-ts, and then subjected to plate culture at 30° C. onto L-agar medium containing 50 mg/L ampicillin, to thereby select ampicillin-resistant strains.

Subsequently, to remove the plasmid pMW-intxis-ts, the cells were subcultured twice at 42° C. on L-agar medium, and ampicillin resistance and chloramphenicol resistance of the resulting colonies were examined, to thereby yield a chloramphenicol- and ampicillin-sensitive strain, in which the cadA gene was disrupted, and att-cat and the pMW-intxis-ts were removed. The strain was named WC196ΔcadA.

(2-2) Disruption of the 1dcC Gene in the WC196ΔcadA Strain

The 1dcC gene in the WC196ΔcadA strain was disrupted by using oligonucleotides of SEQ ID NOS: 11 and 12 as primers in the same way as described above. In this way, a cadA and 1dcC-disrupted strain named WC196ΔcadAΔ1dcC was obtained.

<3>Effect of Amplification of the acs Gene in an L-Lysine-Producing Strain of *Escherichia* Bacterium Introduction of a plasmid for lysine production into the WC196ΔcadAΔ1dcC strain WC196ΔcadAΔ1dcC strain was transformed with a plasmid for lysine production named pCABD2 (WO 01/53459), which carries the dapA gene, dapB gene, lysC gene and ddh gene, to thereby yield the WC196ΔcadAΔ1dcC/pCABD2 strain.

The WC196ΔcadAΔ1dc/pCABD2 strain was transformed with the plasmid for amplifying the acs gene (pMWacs) which was constructed in Example 1 and a control plasmid (pMW119) (Takara Bio Inc), and streptomycin and ampicillin-resistant strains were selected. Introduction of the plasmids was confirmed, and the pMWacs-introduced strain and pMW119-introduced strain were named WC196ΔcadAΔ1dc/pCABD2-acs strain and WC196ΔcadAΔ1dc/pCABD2-119 strain, respectively.

The WC196ΔcadAΔ1dc/pCABD2-acs and WC196ΔcadAΔ1dc/pCABD2-119 strains were cultured at 37° C. in L-medium containing 50 mg/L of amplicillin and 20 mg/L of streptomycin until the final OD600 reached about 0.6, and then an equal volume of 40% glycerol solution was added to the culture, followed by stirring. Then, the resulting suspension was dispensed in appropriate amounts and stored at −80° C., which was used as a glycerol stock.

The glycerol stocks of the strains were thawed, and 100 μL of each strain was uniformly applied on an L-plate containing 50 mg/L ampicillin and 20 mg/L streptomycin, and cultured at 37° C. for 24 hours. About one eighth of the cells of each strain on the plate was inoculated into 20 mL of the fermentation medium (L-lysine production medium for *Escherichia* bacteria) containing 50 mg/L ampicillin and 20 mg/L streptomycin in a 500 mL-Sakaguchi flask and cultured at 37° C. using a reciprocal shaker for 19 hours. The amount of L-lysine which accumulated in the medium was determined using a Biotech Analyzer AS210 (Sakura Seiki Co. Ltd.).

L-lysine Production Medium for *Escherichia* Bacteria:

| | |
|---|---|
| Glucose | 40 g/L |
| Ammonium sulfate | 24 g/L |
| Potassium dihydrogen phosphate | 1.0 g/L |
| Magnesium sulfate heptahydrate | 1.0 g/L |
| Iron sulfate heptahydrate | 0.01 g/L |
| Manganese sulfate heptahydrate | 0.01 g/L |
| Yeast extract | 2.0 g/L |
| Calcium carbonate (Official grade) | 30 g/L (separately sterilized) |

The medium was adjusted to pH 7.0 with potassium hydroxide and sterilized by steam at 115° C. for 10 minutes.

Glucose and magnesium sulfate heptahydrate were separately sterilized.

Calcium carbonate (Official grade) was separately sterilized by heating at 180° C. for 2 hours.

Table 1 shows the amounts of L-lysine present after 19 hours. In the case of the WC196ΔcadAΔ1dc/pCABD2-acs strain, the amount of L-lysine was higher as compared to the WC196ΔcadAΔ1dc/pCABD2-119 strain, which did not contain the acs gene. This data shows that the L-lysine-producing ability was improved by enhancing the expression of the acs gene.

TABLE 1

| Strain | L-lysine accumulation (g/L) | L-lysine yield (%) |
| --- | --- | --- |
| WC196ΔcadAΔldc/pCABD2-119 | 6.4 | 42.9 |
| WC196ΔcadAΔldc/pCABD2-acs | 6.7 | 45.0 |

INDUSTRIAL APPLICABILITY

The bacterium enables efficient fermentative production of basic L-amino acids such as L-lysine, L-ornithine, L-arginine, L-histidine and L-citrulline; aliphatic L-amino acids such as L-isoleucine, L-alanine, L-valine, L-leucine and L-glycine; hydroxy monoaminocarboxylic acids such as L-threonine and L-serine; cyclic L-amino acid such as L-proline; aromatic L-amino acids such as L-phenylalanine, L-tyrosine and L-tryptophan; sulfur-containing L-amino acids such as L-cysteine, L-cystine and L-methionine; and acidic L-amino acids such as L-glutamic acid, L-aspartic acid, L-glutamine and L-asparagine.

While the invention has been described in detail with reference to preferred embodiments thereof, it will be apparent to one skilled in the art that various changes can be made, and equivalents employed, without departing from the scope of the invention. Each of the aforementioned documents is incorporated by reference herein in its entirety.

The invention claimed is:

1. A method of producing L-lysine comprising:
   A) culturing an *Escherichia coli* in a medium, and
   B) collecting the L-lysine from the medium or the *Escherichia coli*,
   wherein the *Escherichia coli* is an L-lysine-producing *Escherichia coli*, and wherein the *Escherichia coli* has been modified to enhance acetyl-CoA synthetase activity by a method selected from the group consisting of:
   a) increasing the copy number of the acs gene which encodes the acetyl-CoA synthetase,
   b) modifying an expression regulatory sequence of said gene, and
   c) combinations thereof, and
   wherein the acs gene is selected from the group consisting of:
   (i) a DNA comprising the nucleotide sequence of SEQ ID NO: 3 and
   (ii) a DNA that hybridizes with a nucleotide sequence which is complementary to the nucleotide sequence of SEQ ID NO: 3 under stringent conditions of washing in 0.1×SSC, 0.1% SDS at 60° C., and wherein said DNA encodes a protein with acetyl-CoA synthetase activity.

* * * * *

SEQUENCE LISTING

```
<160> NUMBER OF SEQ ID NOS: 12

<210> SEQ ID NO 1
<211> LENGTH: 28
<212> TYPE: DNA
<213> ORGANISM: Artificial sequence
<220> FEATURE:
<223> OTHER INFORMATION: 5'-primer for acs

<400> SEQUENCE: 1
cgggatcctc gcatcgggca attgtggg                                       28

<210> SEQ ID NO 2
<211> LENGTH: 30
<212> TYPE: DNA
<213> ORGANISM: Artificial sequence
<220> FEATURE:
<223> OTHER INFORMATION: 3'-primer for acs

<400> SEQUENCE: 2
acgcgtcgac gggcttcatc cgaattgcgc                                     30

<210> SEQ ID NO 3
<211> LENGTH: 1959
<212> TYPE: DNA
<213> ORGANISM: Escherichia coli
<220> FEATURE:
<221> NAME/KEY: CDS
<222> LOCATION: (1)..(1956)

<400> SEQUENCE: 3 atg agc caa att cac aaa cac acc att cct gcc aac atc gca gac cgt      48
Met Ser Gln Ile His Lys His Thr Ile Pro Ala Asn Ile Ala Asp Arg
1               5                   10                  15 tgc ctg ata aac cct cag cag tac gag gcg atg tat caa caa tct att      96
Cys Leu Ile Asn Pro Gln Gln Tyr Glu Ala Met Tyr Gln Gln Ser Ile
            20                  25                  30 aac gta cct gat acc ttc tgg ggc gaa cag gga aaa att ctt gac tgg     144
Asn Val Pro Asp Thr Phe Trp Gly Glu Gln Gly Lys Ile Leu Asp Trp
        35                  40                  45 atc aaa cct tac cag aag gtg aaa aac acc tcc ttt gcc ccc ggt aat     192
Ile Lys Pro Tyr Gln Lys Val Lys Asn Thr Ser Phe Ala Pro Gly Asn
    50                  55                  60
```

-continued

| | | |
|---|---|---|
| gtg tcc att aaa tgg tac gag gac ggc acg ctg aat ctg gcg gca aac<br>Val Ser Ile Lys Trp Tyr Glu Asp Gly Thr Leu Asn Leu Ala Ala Asn<br>65                    70                    75                    80 | 240 |
| tgc ctt gac cgc cat ctg caa gaa aac ggc gat cgt acc gcc atc atc<br>Cys Leu Asp Arg His Leu Gln Glu Asn Gly Asp Arg Thr Ala Ile Ile<br>                   85                    90                    95 | 288 |
| tgg gaa ggc gac gac gcc agc cag agc aaa cat atc agc tat aaa gag<br>Trp Glu Gly Asp Asp Ala Ser Gln Ser Lys His Ile Ser Tyr Lys Glu<br>               100                  105                110 | 336 |
| ctg cac cgc gac gtc tgc cgc ttc gcc aat acc ctg ctc gag ctg ggc<br>Leu His Arg Asp Val Cys Arg Phe Ala Asn Thr Leu Leu Glu Leu Gly<br>      115                  120                  125 | 384 |
| att aaa aaa ggt gat gtg gtg gcg att tat atg ccg atg gtg ccg gaa<br>Ile Lys Lys Gly Asp Val Val Ala Ile Tyr Met Pro Met Val Pro Glu<br>130                    135                  140 | 432 |
| gcc gcg gtt gcg atg ctg gcc tgc gcc cgc att ggc gcg gtg cat tcg<br>Ala Ala Val Ala Met Leu Ala Cys Ala Arg Ile Gly Ala Val His Ser<br>145                    150                  155                160 | 480 |
| gtg att ttc ggc ggc ttc tcg ccg gaa gcc gtt gcc ggg cgc att att<br>Val Ile Phe Gly Gly Phe Ser Pro Glu Ala Val Ala Gly Arg Ile Ile<br>               165                  170                175 | 528 |
| gat tcc aac tca cga ctg gtg atc act tcc gac gaa ggt gtg cgt gcc<br>Asp Ser Asn Ser Arg Leu Val Ile Thr Ser Asp Glu Gly Val Arg Ala<br>                  180                  185                190 | 576 |
| ggg cgc agt att ccg ctg aag aaa aac gtt gat gac gcg ctg aaa aac<br>Gly Arg Ser Ile Pro Leu Lys Lys Asn Val Asp Asp Ala Leu Lys Asn<br>      195                  200                  205 | 624 |
| ccg aac gtc acc agc gta gag cat gtg gtg gta ctg aag cgt act ggc<br>Pro Asn Val Thr Ser Val Glu His Val Val Val Leu Lys Arg Thr Gly<br>210                    215                  220 | 672 |
| ggg aaa att gac tgg cag gaa ggg cgc gac ctg tgg tgg cac gac ctg<br>Gly Lys Ile Asp Trp Gln Glu Gly Arg Asp Leu Trp Trp His Asp Leu<br>225                    230                  235                240 | 720 |
| gtt gag caa gcg agc gat cag cac cag gcg gaa gag atg aac gcc gaa<br>Val Glu Gln Ala Ser Asp Gln His Gln Ala Glu Glu Met Asn Ala Glu<br>                  245                  250                255 | 768 |
| gat ccg ctg ttt att ctc tac acc tcc ggt tct acc ggt aag cca aaa<br>Asp Pro Leu Phe Ile Leu Tyr Thr Ser Gly Ser Thr Gly Lys Pro Lys<br>             260                  265                270 | 816 |
| ggt gtg ctg cat act acc ggc ggt tat ctg gtg tac gcg gcg ctg acc<br>Gly Val Leu His Thr Thr Gly Gly Tyr Leu Val Tyr Ala Ala Leu Thr<br>      275                  280                  285 | 864 |
| ttt aaa tat gtc ttt gat tat cat ccg ggt gat atc tac tgg tgc acc<br>Phe Lys Tyr Val Phe Asp Tyr His Pro Gly Asp Ile Tyr Trp Cys Thr<br>290                    295                  300 | 912 |
| gcc gat gtg ggc tgg gtg acc gga cac agt tac ttg ctg tac ggc ccg<br>Ala Asp Val Gly Trp Val Thr Gly His Ser Tyr Leu Leu Tyr Gly Pro<br>305                    310                  315                320 | 960 |
| ctg gcc tgc ggt gcg acc acg ctg atg ttt gaa ggc gta ccc aac tgg<br>Leu Ala Cys Gly Ala Thr Thr Leu Met Phe Glu Gly Val Pro Asn Trp<br>                  325                  330                335 | 1008 |
| ccg acg cct gcc cgt atg gcg cag gtg gtg gac aag cat cag gtc aat<br>Pro Thr Pro Ala Arg Met Ala Gln Val Val Asp Lys His Gln Val Asn<br>             340                  345                350 | 1056 |
| att ctc tat acc gca ccc acg gcg atc cgc gcg ctg atg gcg gaa ggc<br>Ile Leu Tyr Thr Ala Pro Thr Ala Ile Arg Ala Leu Met Ala Glu Gly<br>      355                  360                  365 | 1104 |
| gat aaa gcg atc gaa ggc acc gac cgt tcg tcg ctg cgc att ctc ggt<br>Asp Lys Ala Ile Glu Gly Thr Asp Arg Ser Ser Leu Arg Ile Leu Gly | 1152 |

-continued

```
                 370                 375                 380
tcc gtg ggc gag cca att aac ccg gaa gcg tgg gag tgg tac tgg aaa    1200
Ser Val Gly Glu Pro Ile Asn Pro Glu Ala Trp Glu Trp Tyr Trp Lys
385                 390                 395                 400 aaa atc ggc aac gag aaa tgt ccg gtg gtc gat acc tgg tgg cag acc    1248
Lys Ile Gly Asn Glu Lys Cys Pro Val Val Asp Thr Trp Trp Gln Thr
                405                 410                 415 gaa acc ggc ggt ttc atg atc acc ccg ctg cct ggc gct acc gag ctg    1296
Glu Thr Gly Gly Phe Met Ile Thr Pro Leu Pro Gly Ala Thr Glu Leu
            420                 425                 430 aaa gcc ggt tcg gca aca cgt ccg ttc ttc ggc gtg caa ccg gcg ctg    1344
Lys Ala Gly Ser Ala Thr Arg Pro Phe Phe Gly Val Gln Pro Ala Leu
        435                 440                 445 gtc gat aac gaa ggt aac ccg ctg gag ggg gcc acc gaa ggt agc ctg    1392
Val Asp Asn Glu Gly Asn Pro Leu Glu Gly Ala Thr Glu Gly Ser Leu
    450                 455                 460 gta atc acc gac tcc tgg ccg ggt cag gcg cgt acg ctg ttt ggc gat    1440
Val Ile Thr Asp Ser Trp Pro Gly Gln Ala Arg Thr Leu Phe Gly Asp
465                 470                 475                 480 cac gaa cgt ttt gaa cag acc tac ttc tcc acc ttc aaa aat atg tat    1488
His Glu Arg Phe Glu Gln Thr Tyr Phe Ser Thr Phe Lys Asn Met Tyr
                485                 490                 495 ttc agc ggc gac ggc gcg cgt cgc gat gaa gat ggc tat tac tgg ata    1536
Phe Ser Gly Asp Gly Ala Arg Arg Asp Glu Asp Gly Tyr Tyr Trp Ile
            500                 505                 510 acc ggg cgt gtg gac gac gtg ctg aac gtc tcc ggt cac cgt ctg ggg    1584
Thr Gly Arg Val Asp Asp Val Leu Asn Val Ser Gly His Arg Leu Gly
        515                 520                 525 acg gca gag att gag tcg gcg ctg gtg gcg cat ccg aag att gcc gaa    1632
Thr Ala Glu Ile Glu Ser Ala Leu Val Ala His Pro Lys Ile Ala Glu
    530                 535                 540 gcc gcc gta gta ggt att ccg cac aat att aaa ggt cag gcg atc tac    1680
Ala Ala Val Val Gly Ile Pro His Asn Ile Lys Gly Gln Ala Ile Tyr
545                 550                 555                 560 gcc tac gtc acg ctt aat cac ggg gag gaa ccg tca cca gaa ctg tac    1728
Ala Tyr Val Thr Leu Asn His Gly Glu Glu Pro Ser Pro Glu Leu Tyr
                565                 570                 575 gca gaa gtc cgc aac tgg gtg cgt aaa gag att ggc ccg ctg gcg acg    1776
Ala Glu Val Arg Asn Trp Val Arg Lys Glu Ile Gly Pro Leu Ala Thr
            580                 585                 590 cca gac gtg ctg cac tgg acc gac tcc ctg cct aaa acc cgc tcc ggc    1824
Pro Asp Val Leu His Trp Thr Asp Ser Leu Pro Lys Thr Arg Ser Gly
        595                 600                 605 aaa att atg cgc cgt att ctg cgc aaa att gcg gcg ggc gat acc agc    1872
Lys Ile Met Arg Arg Ile Leu Arg Lys Ile Ala Ala Gly Asp Thr Ser
    610                 615                 620 aac ctg ggc gat acc tcg acg ctt gcc gat cct ggc gta gtc gag aag    1920
Asn Leu Gly Asp Thr Ser Thr Leu Ala Asp Pro Gly Val Val Glu Lys
625                 630                 635                 640 ctg ctt gaa gag aag cag gct atc gcg atg cca tcg taa                1959
Leu Leu Glu Glu Lys Gln Ala Ile Ala Met Pro Ser
                645                 650
```

<210> SEQ ID NO 4
<211> LENGTH: 652
<212> TYPE: PRT
<213> ORGANISM: Escherichia coli

<400> SEQUENCE: 4

Met Ser Gln Ile His Lys His Thr Ile Pro Ala Asn Ile Ala Asp Arg

-continued

```
1               5                   10                  15

Cys Leu Ile Asn Pro Gln Gln Tyr Glu Ala Met Tyr Gln Gln Ser Ile
            20                  25                  30

Asn Val Pro Asp Thr Phe Trp Gly Glu Gln Gly Lys Ile Leu Asp Trp
            35                  40                  45

Ile Lys Pro Tyr Gln Lys Val Lys Asn Thr Ser Phe Ala Pro Gly Asn
 50                  55                  60

Val Ser Ile Lys Trp Tyr Glu Asp Gly Thr Leu Asn Leu Ala Ala Asn
 65                  70                  75                  80

Cys Leu Asp Arg His Leu Gln Glu Asn Gly Asp Arg Thr Ala Ile Ile
                85                  90                  95

Trp Glu Gly Asp Asp Ala Ser Gln Ser Lys His Ile Ser Tyr Lys Glu
                100                 105                 110

Leu His Arg Asp Val Cys Arg Phe Ala Asn Thr Leu Leu Glu Leu Gly
            115                 120                 125

Ile Lys Lys Gly Asp Val Val Ala Ile Tyr Met Pro Met Val Pro Glu
            130                 135                 140

Ala Ala Val Ala Met Leu Ala Cys Ala Arg Ile Gly Ala Val His Ser
145                 150                 155                 160

Val Ile Phe Gly Gly Phe Ser Pro Glu Ala Val Ala Gly Arg Ile Ile
                165                 170                 175

Asp Ser Asn Ser Arg Leu Val Ile Thr Ser Asp Glu Gly Val Arg Ala
            180                 185                 190

Gly Arg Ser Ile Pro Leu Lys Lys Asn Val Asp Asp Ala Leu Lys Asn
            195                 200                 205

Pro Asn Val Thr Ser Val Glu His Val Val Leu Lys Arg Thr Gly
            210                 215                 220

Gly Lys Ile Asp Trp Gln Glu Gly Arg Asp Leu Trp Trp His Asp Leu
225                 230                 235                 240

Val Glu Gln Ala Ser Asp Gln His Gln Ala Glu Met Asn Ala Glu
                245                 250                 255

Asp Pro Leu Phe Ile Leu Tyr Thr Ser Gly Ser Thr Gly Lys Pro Lys
            260                 265                 270

Gly Val Leu His Thr Thr Gly Gly Tyr Leu Val Tyr Ala Ala Leu Thr
            275                 280                 285

Phe Lys Tyr Val Phe Asp Tyr His Pro Gly Asp Ile Tyr Trp Cys Thr
            290                 295                 300

Ala Asp Val Gly Trp Val Thr Gly His Ser Tyr Leu Leu Tyr Gly Pro
305                 310                 315                 320

Leu Ala Cys Gly Ala Thr Thr Leu Met Phe Glu Gly Val Pro Asn Trp
                325                 330                 335

Pro Thr Pro Ala Arg Met Ala Gln Val Val Asp Lys His Gln Val Asn
            340                 345                 350

Ile Leu Tyr Thr Ala Pro Thr Ala Ile Arg Ala Leu Met Ala Glu Gly
            355                 360                 365

Asp Lys Ala Ile Glu Gly Thr Asp Arg Ser Ser Leu Arg Ile Leu Gly
            370                 375                 380

Ser Val Gly Glu Pro Ile Asn Pro Glu Ala Trp Glu Trp Tyr Trp Lys
385                 390                 395                 400

Lys Ile Gly Asn Glu Lys Cys Pro Val Val Asp Thr Trp Trp Gln Thr
                405                 410                 415

Glu Thr Gly Gly Phe Met Ile Thr Pro Leu Pro Gly Ala Thr Glu Leu
            420                 425                 430
```

-continued

```
Lys Ala Gly Ser Ala Thr Arg Pro Phe Phe Gly Val Gln Pro Ala Leu
        435                 440                 445

Val Asp Asn Glu Gly Asn Pro Leu Glu Gly Ala Thr Glu Gly Ser Leu
    450                 455                 460

Val Ile Thr Asp Ser Trp Pro Gly Gln Ala Arg Thr Leu Phe Gly Asp
465                 470                 475                 480

His Glu Arg Phe Glu Gln Thr Tyr Phe Ser Thr Phe Lys Asn Met Tyr
                485                 490                 495

Phe Ser Gly Asp Gly Ala Arg Arg Asp Glu Asp Gly Tyr Tyr Trp Ile
            500                 505                 510

Thr Gly Arg Val Asp Asp Val Leu Asn Val Ser Gly His Arg Leu Gly
        515                 520                 525

Thr Ala Glu Ile Glu Ser Ala Leu Val Ala His Pro Lys Ile Ala Glu
    530                 535                 540

Ala Ala Val Val Gly Ile Pro His Asn Ile Lys Gly Gln Ala Ile Tyr
545                 550                 555                 560

Ala Tyr Val Thr Leu Asn His Gly Glu Glu Pro Ser Pro Glu Leu Tyr
                565                 570                 575

Ala Glu Val Arg Asn Trp Val Arg Lys Glu Ile Gly Pro Leu Ala Thr
            580                 585                 590

Pro Asp Val Leu His Trp Thr Asp Ser Leu Pro Lys Thr Arg Ser Gly
        595                 600                 605

Lys Ile Met Arg Arg Ile Leu Arg Lys Ile Ala Ala Gly Asp Thr Ser
    610                 615                 620

Asn Leu Gly Asp Thr Ser Thr Leu Ala Asp Pro Gly Val Val Glu Lys
625                 630                 635                 640

Leu Leu Glu Glu Lys Gln Ala Ile Ala Met Pro Ser
                645                 650

<210> SEQ ID NO 5
<211> LENGTH: 2148
<212> TYPE: DNA
<213> ORGANISM: Escherichia coli
<220> FEATURE:
<221> NAME/KEY: CDS
<222> LOCATION: (1)..(2145)

<400> SEQUENCE: 5 atg aac gtt att gca ata ttg aat cac atg ggg gtt tat ttt aaa gaa    48
Met Asn Val Ile Ala Ile Leu Asn His Met Gly Val Tyr Phe Lys Glu
1               5                   10                  15 gaa ccc atc cgt gaa ctt cat cgc gcg ctt gaa cgt ctg aac ttc cag    96
Glu Pro Ile Arg Glu Leu His Arg Ala Leu Glu Arg Leu Asn Phe Gln
                20                  25                  30 att gtt tac ccg aac gac cgt gac gac tta tta aaa ctg atc gaa aac    144
Ile Val Tyr Pro Asn Asp Arg Asp Asp Leu Leu Lys Leu Ile Glu Asn
            35                  40                  45 aat gcg cgt ctg tgc ggc gtt att ttt gac tgg gat aaa tat aat ctc    192
Asn Ala Arg Leu Cys Gly Val Ile Phe Asp Trp Asp Lys Tyr Asn Leu
        50                  55                  60 gag ctg tgc gaa gaa att agc aaa atg aac gag aac ctg ccg ttg tac    240
Glu Leu Cys Glu Glu Ile Ser Lys Met Asn Glu Asn Leu Pro Leu Tyr
65                  70                  75                  80 gcg ttc gct aat acg tat tcc act ctc gat gta agc ctg aat gac ctg    288
Ala Phe Ala Asn Thr Tyr Ser Thr Leu Asp Val Ser Leu Asn Asp Leu
                85                  90                  95 cgt tta cag att agc ttc ttt gaa tat gcg ctg ggt gct gct gaa gat    336
```

```
Arg Leu Gln Ile Ser Phe Phe Glu Tyr Ala Leu Gly Ala Ala Glu Asp
            100                 105                 110 att gct aat aag atc aag cag acc act gac gaa tat atc aac act att      384
Ile Ala Asn Lys Ile Lys Gln Thr Thr Asp Glu Tyr Ile Asn Thr Ile
            115                 120                 125 ctg cct ccg ctg act aaa gca ctg ttt aaa tat gtt cgt gaa ggt aaa      432
Leu Pro Pro Leu Thr Lys Ala Leu Phe Lys Tyr Val Arg Glu Gly Lys
        130                 135                 140 tat act ttc tgt act cct ggt cac atg ggc ggt act gca ttc cag aaa      480
Tyr Thr Phe Cys Thr Pro Gly His Met Gly Gly Thr Ala Phe Gln Lys
145                 150                 155                 160 agc ccg gta ggt agc ctg ttc tat gat ttc ttt ggt ccg aat acc atg      528
Ser Pro Val Gly Ser Leu Phe Tyr Asp Phe Phe Gly Pro Asn Thr Met
                165                 170                 175 aaa tct gat att tcc att tca gta tct gaa ctg ggt tct ctg ctg gat      576
Lys Ser Asp Ile Ser Ile Ser Val Ser Glu Leu Gly Ser Leu Leu Asp
            180                 185                 190 cac agt ggt cca cac aaa gaa gca gaa cag tat atc gct cgc gtc ttt      624
His Ser Gly Pro His Lys Glu Ala Glu Gln Tyr Ile Ala Arg Val Phe
        195                 200                 205 aac gca gac cgc agc tac atg gtg acc aac ggt act tcc act gcg aac      672
Asn Ala Asp Arg Ser Tyr Met Val Thr Asn Gly Thr Ser Thr Ala Asn
210                 215                 220 aaa att gtt ggt atg tac tct gct cca gca ggc agc acc att ctg att      720
Lys Ile Val Gly Met Tyr Ser Ala Pro Ala Gly Ser Thr Ile Leu Ile
225                 230                 235                 240 gac cgt aac tgc cac aaa tcg ctg acc cac ctg atg atg atg agc gat      768
Asp Arg Asn Cys His Lys Ser Leu Thr His Leu Met Met Met Ser Asp
                245                 250                 255 gtt acg cca atc tat ttc cgc ccg acc cgt aac gct tac ggt att ctt      816
Val Thr Pro Ile Tyr Phe Arg Pro Thr Arg Asn Ala Tyr Gly Ile Leu
            260                 265                 270 ggt ggt atc cca cag agt gaa ttc cag cac gct acc att gct aag cgc      864
Gly Gly Ile Pro Gln Ser Glu Phe Gln His Ala Thr Ile Ala Lys Arg
        275                 280                 285 gtg aaa gaa aca cca aac gca acc tgg ccg gta cat gct gta att acc      912
Val Lys Glu Thr Pro Asn Ala Thr Trp Pro Val His Ala Val Ile Thr
290                 295                 300 aac tct acc tat gat ggt ctg ctg tac aac acc gac ttc atc aag aaa      960
Asn Ser Thr Tyr Asp Gly Leu Leu Tyr Asn Thr Asp Phe Ile Lys Lys
305                 310                 315                 320 aca ctg gat gtg aaa tcc atc cac ttt gac tcc gcg tgg gtg cct tac     1008
Thr Leu Asp Val Lys Ser Ile His Phe Asp Ser Ala Trp Val Pro Tyr
                325                 330                 335 acc aac ttc tca ccg att tac gaa ggt aaa tgc ggt atg agc ggt ggc     1056
Thr Asn Phe Ser Pro Ile Tyr Glu Gly Lys Cys Gly Met Ser Gly Gly
            340                 345                 350 cgt gta gaa ggg aaa gtg att tac gaa acc cag tcc act cac aaa ctg     1104
Arg Val Glu Gly Lys Val Ile Tyr Glu Thr Gln Ser Thr His Lys Leu
        355                 360                 365 ctg gcg gcg ttc tct cag gct tcc atg atc cac gtt aaa ggt gac gta     1152
Leu Ala Ala Phe Ser Gln Ala Ser Met Ile His Val Lys Gly Asp Val
370                 375                 380 aac gaa gaa acc ttt aac gaa gcc tac atg atg cac acc acc act tct     1200
Asn Glu Glu Thr Phe Asn Glu Ala Tyr Met Met His Thr Thr Thr Ser
385                 390                 395                 400 ccg cac tac ggt atc gtg gcg tcc act gaa acc gct gcg gcg atg atg     1248
Pro His Tyr Gly Ile Val Ala Ser Thr Glu Thr Ala Ala Ala Met Met
                405                 410                 415
```

```
aaa ggc aat gca ggt aag cgt ctg atc aac ggt tct att gaa cgt gcg    1296
Lys Gly Asn Ala Gly Lys Arg Leu Ile Asn Gly Ser Ile Glu Arg Ala
            420                 425                 430 atc aaa ttc cgt aaa gag atc aaa cgt ctg aga acg gaa tct gat ggc    1344
Ile Lys Phe Arg Lys Glu Ile Lys Arg Leu Arg Thr Glu Ser Asp Gly
        435                 440                 445 tgg ttc ttt gat gta tgg cag ccg gat cat atc gat acg act gaa tgc    1392
Trp Phe Phe Asp Val Trp Gln Pro Asp His Ile Asp Thr Thr Glu Cys
    450                 455                 460 tgg ccg ctg cgt tct gac agc acc tgg cac ggc ttc aaa aac atc gat    1440
Trp Pro Leu Arg Ser Asp Ser Thr Trp His Gly Phe Lys Asn Ile Asp
465                 470                 475                 480 aac gag cac atg tat ctt gac ccg atc aaa gtc acc ctg ctg act ccg    1488
Asn Glu His Met Tyr Leu Asp Pro Ile Lys Val Thr Leu Leu Thr Pro
                485                 490                 495 ggg atg gaa aaa gac ggc acc atg agc gac ttt ggt att ccg gcc agc    1536
Gly Met Glu Lys Asp Gly Thr Met Ser Asp Phe Gly Ile Pro Ala Ser
            500                 505                 510 atc gtg gcg aaa tac ctc gac gaa cat ggc atc gtt gtt gag aaa acc    1584
Ile Val Ala Lys Tyr Leu Asp Glu His Gly Ile Val Val Glu Lys Thr
        515                 520                 525 ggt ccg tat aac ctg ctg ttc ctg ttc agc atc ggt atc gat aag acc    1632
Gly Pro Tyr Asn Leu Leu Phe Leu Phe Ser Ile Gly Ile Asp Lys Thr
    530                 535                 540 aaa gca ctg agc ctg ctg cgt gct ctg act gac ttt aaa cgt gcg ttc    1680
Lys Ala Leu Ser Leu Leu Arg Ala Leu Thr Asp Phe Lys Arg Ala Phe
545                 550                 555                 560 gac ctg aac ctg cgt gtg aaa aac atg ctg ccg tct ctg tat cgt gaa    1728
Asp Leu Asn Leu Arg Val Lys Asn Met Leu Pro Ser Leu Tyr Arg Glu
                565                 570                 575 gat cct gaa ttc tat gaa aac atg cgt att cag gaa ctg gct cag aat    1776
Asp Pro Glu Phe Tyr Glu Asn Met Arg Ile Gln Glu Leu Ala Gln Asn
            580                 585                 590 atc cac aaa ctg att gtt cac cac aat ctg ccg gat ctg atg tat cgc    1824
Ile His Lys Leu Ile Val His His Asn Leu Pro Asp Leu Met Tyr Arg
        595                 600                 605 gca ttt gaa gtg ctg ccg acg atg gta atg act ccg tat gct gca ttc    1872
Ala Phe Glu Val Leu Pro Thr Met Val Met Thr Pro Tyr Ala Ala Phe
    610                 615                 620 cag aaa gag ctg cac ggt atg acc gaa gaa gtt tac ctc gac gaa atg    1920
Gln Lys Glu Leu His Gly Met Thr Glu Glu Val Tyr Leu Asp Glu Met
625                 630                 635                 640 gta ggt cgt att aac gcc aat atg atc ctt ccg tac ccg ccg gga gtt    1968
Val Gly Arg Ile Asn Ala Asn Met Ile Leu Pro Tyr Pro Pro Gly Val
                645                 650                 655 cct ctg gta atg ccg ggt gaa atg atc acc gaa gaa agc cgt ccg gtt    2016
Pro Leu Val Met Pro Gly Glu Met Ile Thr Glu Glu Ser Arg Pro Val
            660                 665                 670 ctg gag ttc ctg cag atg ctg tgt gaa atc ggc gct cac tat ccg ggc    2064
Leu Glu Phe Leu Gln Met Leu Cys Glu Ile Gly Ala His Tyr Pro Gly
        675                 680                 685 ttt gaa acc gat att cac ggt gca tac cgt cag gct gat ggc cgc tat    2112
Phe Glu Thr Asp Ile His Gly Ala Tyr Arg Gln Ala Asp Gly Arg Tyr
    690                 695                 700 acc gtt aag gta ttg aaa gaa gaa agc aaa aaa taa                    2148
Thr Val Lys Val Leu Lys Glu Glu Ser Lys Lys
705                 710                 715

<210> SEQ ID NO 6
<211> LENGTH: 715
```

```
<212> TYPE: PRT
<213> ORGANISM: Escherichia coli

<400> SEQUENCE: 6
```

| | | | | | | | | | | | | | | |
|---|---|---|---|---|---|---|---|---|---|---|---|---|---|---|
| Met | Asn | Val | Ile | Ala | Ile | Leu | Asn | His | Met | Gly | Val | Tyr | Phe | Lys | Glu |
| 1 | | | | 5 | | | | | 10 | | | | | 15 | |

```
Met Asn Val Ile Ala Ile Leu Asn His Met Gly Val Tyr Phe Lys Glu
1               5                   10                  15

Glu Pro Ile Arg Glu Leu His Arg Ala Leu Glu Arg Leu Asn Phe Gln
                20                  25                  30

Ile Val Tyr Pro Asn Asp Arg Asp Leu Leu Lys Leu Ile Glu Asn
                35                  40                  45

Asn Ala Arg Leu Cys Gly Val Ile Phe Asp Trp Asp Lys Tyr Asn Leu
        50                  55                  60

Glu Leu Cys Glu Glu Ile Ser Lys Met Asn Glu Asn Leu Pro Leu Tyr
65                      70                  75                  80

Ala Phe Ala Asn Thr Tyr Ser Thr Leu Asp Val Ser Leu Asn Asp Leu
                    85                  90                  95

Arg Leu Gln Ile Ser Phe Phe Glu Tyr Ala Leu Gly Ala Ala Glu Asp
                100                 105                 110

Ile Ala Asn Lys Ile Lys Gln Thr Thr Asp Glu Tyr Ile Asn Thr Ile
                115                 120                 125

Leu Pro Pro Leu Thr Lys Ala Leu Phe Lys Tyr Val Arg Glu Gly Lys
        130                 135                 140

Tyr Thr Phe Cys Thr Pro Gly His Met Gly Gly Thr Ala Phe Gln Lys
145                 150                 155                 160

Ser Pro Val Gly Ser Leu Phe Tyr Asp Phe Phe Gly Pro Asn Thr Met
                165                 170                 175

Lys Ser Asp Ile Ser Ile Ser Val Ser Glu Leu Gly Ser Leu Leu Asp
                180                 185                 190

His Ser Gly Pro His Lys Glu Ala Glu Gln Tyr Ile Ala Arg Val Phe
            195                 200                 205

Asn Ala Asp Arg Ser Tyr Met Val Thr Asn Gly Thr Ser Thr Ala Asn
        210                 215                 220

Lys Ile Val Gly Met Tyr Ser Ala Pro Ala Gly Ser Thr Ile Leu Ile
225                 230                 235                 240

Asp Arg Asn Cys His Lys Ser Leu Thr His Leu Met Met Met Ser Asp
                245                 250                 255

Val Thr Pro Ile Tyr Phe Arg Pro Thr Arg Asn Ala Tyr Gly Ile Leu
                260                 265                 270

Gly Gly Ile Pro Gln Ser Glu Phe Gln His Ala Thr Ile Ala Lys Arg
            275                 280                 285

Val Lys Glu Thr Pro Asn Ala Thr Trp Pro Val His Ala Val Ile Thr
        290                 295                 300

Asn Ser Thr Tyr Asp Gly Leu Leu Tyr Asn Thr Asp Phe Ile Lys Lys
305                 310                 315                 320

Thr Leu Asp Val Lys Ser Ile His Phe Asp Ser Ala Trp Val Pro Tyr
                325                 330                 335

Thr Asn Phe Ser Pro Ile Tyr Glu Gly Lys Cys Gly Met Ser Gly Gly
            340                 345                 350

Arg Val Glu Gly Lys Val Ile Tyr Glu Thr Gln Ser Thr His Lys Leu
            355                 360                 365

Leu Ala Ala Phe Ser Gln Ala Ser Met Ile His Val Lys Gly Asp Val
        370                 375                 380

Asn Glu Glu Thr Phe Asn Glu Ala Tyr Met Met His Thr Thr Thr Ser
385                 390                 395                 400
```

```
Pro His Tyr Gly Ile Val Ala Ser Thr Glu Thr Ala Ala Met Met
                405                 410                 415

Lys Gly Asn Ala Gly Lys Arg Leu Ile Asn Gly Ser Ile Glu Arg Ala
            420                 425                 430

Ile Lys Phe Arg Lys Glu Ile Lys Arg Leu Arg Thr Glu Ser Asp Gly
        435                 440                 445

Trp Phe Asp Val Trp Gln Pro Asp His Ile Asp Thr Thr Glu Cys
    450                 455                 460

Trp Pro Leu Arg Ser Asp Ser Thr Trp His Gly Phe Lys Asn Ile Asp
465                 470                 475                 480

Asn Glu His Met Tyr Leu Asp Pro Ile Lys Val Thr Leu Leu Thr Pro
                485                 490                 495

Gly Met Glu Lys Asp Gly Thr Met Ser Asp Phe Gly Ile Pro Ala Ser
            500                 505                 510

Ile Val Ala Lys Tyr Leu Asp Glu His Gly Ile Val Val Glu Lys Thr
        515                 520                 525

Gly Pro Tyr Asn Leu Leu Phe Leu Phe Ser Ile Gly Ile Asp Lys Thr
    530                 535                 540

Lys Ala Leu Ser Leu Leu Arg Ala Leu Thr Asp Phe Lys Arg Ala Phe
545                 550                 555                 560

Asp Leu Asn Leu Arg Val Lys Asn Met Leu Pro Ser Leu Tyr Arg Glu
                565                 570                 575

Asp Pro Glu Phe Tyr Glu Asn Met Arg Ile Gln Glu Leu Ala Gln Asn
            580                 585                 590

Ile His Lys Leu Ile Val His His Asn Leu Pro Asp Leu Met Tyr Arg
        595                 600                 605

Ala Phe Glu Val Leu Pro Thr Met Val Met Thr Pro Tyr Ala Ala Phe
    610                 615                 620

Gln Lys Glu Leu His Gly Met Thr Glu Glu Val Tyr Leu Asp Glu Met
625                 630                 635                 640

Val Gly Arg Ile Asn Ala Asn Met Ile Leu Pro Tyr Pro Pro Gly Val
                645                 650                 655

Pro Leu Val Met Pro Gly Glu Met Ile Thr Glu Glu Ser Arg Pro Val
            660                 665                 670

Leu Glu Phe Leu Gln Met Leu Cys Glu Ile Gly Ala His Tyr Pro Gly
        675                 680                 685

Phe Glu Thr Asp Ile His Gly Ala Tyr Arg Gln Ala Asp Gly Arg Tyr
    690                 695                 700

Thr Val Lys Val Leu Lys Glu Ser Lys Lys
705                 710                 715

<210> SEQ ID NO 7
<211> LENGTH: 2142
<212> TYPE: DNA
<213> ORGANISM: Escherichia coli
<220> FEATURE:
<221> NAME/KEY: CDS
<222> LOCATION: (1)..(2139)

<400> SEQUENCE: 7 atg aac atc att gcc att atg gga ccg cat ggc gtc ttt tat aaa gat     48
Met Asn Ile Ile Ala Ile Met Gly Pro His Gly Val Phe Tyr Lys Asp
1               5                   10                  15 gag ccc atc aaa gaa ctg gag tcg gcg ctg gtg gcg caa ggc ttt cag     96
Glu Pro Ile Lys Glu Leu Glu Ser Ala Leu Val Ala Gln Gly Phe Gln
            20                  25                  30
```

```
att atc tgg cca caa aac agc gtt gat ttg ctg aaa ttt atc gag cat        144
Ile Ile Trp Pro Gln Asn Ser Val Asp Leu Leu Lys Phe Ile Glu His
        35                  40                  45 aac cct cga att tgc ggc gtg att ttt gac tgg gat gag tac agt ctc        192
Asn Pro Arg Ile Cys Gly Val Ile Phe Asp Trp Asp Glu Tyr Ser Leu
 50                  55                  60 gat tta tgt agc gat atc aat cag ctt aat gaa tat ctc ccg ctt tat        240
Asp Leu Cys Ser Asp Ile Asn Gln Leu Asn Glu Tyr Leu Pro Leu Tyr
 65                  70                  75                  80 gcc ttc atc aac acc cac tcg acg atg gat gtc agc gtg cag gat atg        288
Ala Phe Ile Asn Thr His Ser Thr Met Asp Val Ser Val Gln Asp Met
                 85                  90                  95 cgg atg gcg ctc tgg ttt ttt gaa tat gcg ctg ggg cag gcg gaa gat        336
Arg Met Ala Leu Trp Phe Phe Glu Tyr Ala Leu Gly Gln Ala Glu Asp
            100                 105                 110 atc gcc att cgt atg cgt cag tac acc gac gaa tat ctt gat aac att        384
Ile Ala Ile Arg Met Arg Gln Tyr Thr Asp Glu Tyr Leu Asp Asn Ile
        115                 120                 125 aca ccg ccg ttc acg aaa gcc ttg ttt acc tac gtc aaa gag cgg aag        432
Thr Pro Pro Phe Thr Lys Ala Leu Phe Thr Tyr Val Lys Glu Arg Lys
130                 135                 140 tac acc ttt tgt acg ccg ggg cat atg ggc ggc acc gca tat caa aaa        480
Tyr Thr Phe Cys Thr Pro Gly His Met Gly Gly Thr Ala Tyr Gln Lys
145                 150                 155                 160 agc ccg gtt ggc tgt ctg ttt tat gat ttt ttc ggc ggg aat act ctt        528
Ser Pro Val Gly Cys Leu Phe Tyr Asp Phe Phe Gly Gly Asn Thr Leu
                165                 170                 175 aag gct gat gtc tct att tcg gtc acc gag ctt ggt tcg ttg ctc gac        576
Lys Ala Asp Val Ser Ile Ser Val Thr Glu Leu Gly Ser Leu Leu Asp
            180                 185                 190 cac acc ggg cca cac ctg gaa gcg gaa gag tac atc gcg cgg act ttt        624
His Thr Gly Pro His Leu Glu Ala Glu Glu Tyr Ile Ala Arg Thr Phe
        195                 200                 205 ggc gcg gaa cag agt tat atc gtt acc aac gga aca tcg acg tcg aac        672
Gly Ala Glu Gln Ser Tyr Ile Val Thr Asn Gly Thr Ser Thr Ser Asn
    210                 215                 220 aaa att gtg ggt atg tac gcc gcg cca tcc ggc agt acg ctg ttg atc        720
Lys Ile Val Gly Met Tyr Ala Ala Pro Ser Gly Ser Thr Leu Leu Ile
225                 230                 235                 240 gac cgc aat tgt cat aaa tcg ctg gcg cat ctg ttg atg atg aac gat        768
Asp Arg Asn Cys His Lys Ser Leu Ala His Leu Leu Met Met Asn Asp
                245                 250                 255 gta gtg cca gtc tgg ctg aaa ccg acg cgt aat gcg ttg ggg att ctt        816
Val Val Pro Val Trp Leu Lys Pro Thr Arg Asn Ala Leu Gly Ile Leu
            260                 265                 270 ggt ggg atc ccg cgc cgt gaa ttt act cgc gac agc atc gaa gag aaa        864
Gly Gly Ile Pro Arg Arg Glu Phe Thr Arg Asp Ser Ile Glu Glu Lys
        275                 280                 285 gtc gct gct acc acg caa gca caa tgg ccg gtt cat gcg gtg atc acc        912
Val Ala Ala Thr Thr Gln Ala Gln Trp Pro Val His Ala Val Ile Thr
    290                 295                 300 aac tcc acc tat gat ggc ttg ctc tac aac acc gac tgg atc aaa cag        960
Asn Ser Thr Tyr Asp Gly Leu Leu Tyr Asn Thr Asp Trp Ile Lys Gln
305                 310                 315                 320 acg ctg gat gtc ccg tcg att cac ttc gat tct gcc tgg gtg ccg tac       1008
Thr Leu Asp Val Pro Ser Ile His Phe Asp Ser Ala Trp Val Pro Tyr
                325                 330                 335 acc cat ttt cat ccg atc tac cag ggt aaa agt ggt atg agc ggc gag       1056
Thr His Phe His Pro Ile Tyr Gln Gly Lys Ser Gly Met Ser Gly Glu
```

-continued

```
                    340                 345                 350
cgt gtt gcg gga aaa gtg atc ttc gaa acg caa tcg acc cac aaa atg      1104
Arg Val Ala Gly Lys Val Ile Phe Glu Thr Gln Ser Thr His Lys Met
            355                 360                 365 ctg gcg gcg tta tcg cag gct tcg ctg atc cac att aaa ggc gag tat      1152
Leu Ala Ala Leu Ser Gln Ala Ser Leu Ile His Ile Lys Gly Glu Tyr
    370                 375                 380 gac gaa gag gcc ttt aac gaa gcc ttt atg atg cat acc acc acc tcg      1200
Asp Glu Glu Ala Phe Asn Glu Ala Phe Met Met His Thr Thr Thr Ser
385                 390                 395                 400 ccc agt tat ccc att gtt gct tcg gtt gag acg gcg gcg gcg atg ctg      1248
Pro Ser Tyr Pro Ile Val Ala Ser Val Glu Thr Ala Ala Ala Met Leu
                405                 410                 415 cgt ggt aat ccg ggc aaa cgg ctg att aac cgt tca gta gaa cga gct      1296
Arg Gly Asn Pro Gly Lys Arg Leu Ile Asn Arg Ser Val Glu Arg Ala
            420                 425                 430 ctg cat ttt cgc aaa gag gtc cag cgg ctg cgg gaa gag tct gac ggt      1344
Leu His Phe Arg Lys Glu Val Gln Arg Leu Arg Glu Glu Ser Asp Gly
        435                 440                 445 tgg ttt ttc gat atc tgg caa ccg ccg cag gtg gat gaa gcc gaa tgc      1392
Trp Phe Phe Asp Ile Trp Gln Pro Pro Gln Val Asp Glu Ala Glu Cys
    450                 455                 460 tgg ccc gtt gcg cct ggc gaa cag tgg cac ggc ttt aac gat gcg gat      1440
Trp Pro Val Ala Pro Gly Glu Gln Trp His Gly Phe Asn Asp Ala Asp
465                 470                 475                 480 gcc gat cat atg ttt ctc gat ccg gtt aaa gtc act att ttg aca ccg      1488
Ala Asp His Met Phe Leu Asp Pro Val Lys Val Thr Ile Leu Thr Pro
                485                 490                 495 ggg atg gac gag cag ggc aat atg agc gag gag ggg atc ccg gcg gcg      1536
Gly Met Asp Glu Gln Gly Asn Met Ser Glu Glu Gly Ile Pro Ala Ala
            500                 505                 510 ctg gta gca aaa ttc ctc gac gaa cgt ggg atc gta gta gag aaa acc      1584
Leu Val Ala Lys Phe Leu Asp Glu Arg Gly Ile Val Val Glu Lys Thr
        515                 520                 525 ggc cct tat aac ctg ctg ttt ctc ttt agt att ggc atc gat aaa acc      1632
Gly Pro Tyr Asn Leu Leu Phe Leu Phe Ser Ile Gly Ile Asp Lys Thr
    530                 535                 540 aaa gca atg gga tta ttg cgt ggg ttg acg gaa ttc aaa cgc tct tac      1680
Lys Ala Met Gly Leu Leu Arg Gly Leu Thr Glu Phe Lys Arg Ser Tyr
545                 550                 555                 560 gat ctc aac ctg cgg atc aaa aat atg cta ccc gat ctc tat gca gaa      1728
Asp Leu Asn Leu Arg Ile Lys Asn Met Leu Pro Asp Leu Tyr Ala Glu
                565                 570                 575 gat ccc gat ttc tac cgc aat atg cgt att cag gat ctg gca caa ggg      1776
Asp Pro Asp Phe Tyr Arg Asn Met Arg Ile Gln Asp Leu Ala Gln Gly
            580                 585                 590 atc cat aag ctg att cgt aaa cac gat ctt ccc ggt ttg atg ttg cgg      1824
Ile His Lys Leu Ile Arg Lys His Asp Leu Pro Gly Leu Met Leu Arg
        595                 600                 605 gca ttc gat act ttg ccg gag atg atc atg acg cca cat cag gca tgg      1872
Ala Phe Asp Thr Leu Pro Glu Met Ile Met Thr Pro His Gln Ala Trp
    610                 615                 620 caa cga caa att aaa ggc gaa gta gaa acc att gcg ctg gaa caa ctg      1920
Gln Arg Gln Ile Lys Gly Glu Val Glu Thr Ile Ala Leu Glu Gln Leu
625                 630                 635                 640 gtc ggt aga gta tcg gca aat atg atc ctg cct tat cca ccg ggc gta      1968
Val Gly Arg Val Ser Ala Asn Met Ile Leu Pro Tyr Pro Pro Gly Val
                645                 650                 655 ccg ctg ttg atg cct gga gaa atg ctg acc aaa gag agc cgc aca gta      2016
```

```
Pro Leu Leu Met Pro Gly Glu Met Leu Thr Lys Glu Ser Arg Thr Val
            660                 665                 670 ctc gat ttt cta ctg atg ctt tgt tcc gtc ggg caa cat tac ccc ggt    2064
Leu Asp Phe Leu Leu Met Leu Cys Ser Val Gly Gln His Tyr Pro Gly
        675                 680                 685 ttt gaa acg gat att cac ggc gcg aaa cag gac gaa gac ggc gtt tac    2112
Phe Glu Thr Asp Ile His Gly Ala Lys Gln Asp Glu Asp Gly Val Tyr
690                 695                 700 cgc gta cga gtc cta aaa atg gcg gga taa                            2142
Arg Val Arg Val Leu Lys Met Ala Gly
705                 710
```

<210> SEQ ID NO 8
<211> LENGTH: 713
<212> TYPE: PRT
<213> ORGANISM: Escherichia coli

<400> SEQUENCE: 8

```
Met Asn Ile Ile Ala Ile Met Gly Pro His Gly Val Phe Tyr Lys Asp
1               5                   10                  15

Glu Pro Ile Lys Glu Leu Glu Ser Ala Leu Val Ala Gln Gly Phe Gln
            20                  25                  30

Ile Ile Trp Pro Gln Asn Ser Val Asp Leu Leu Lys Phe Ile Glu His
        35                  40                  45

Asn Pro Arg Ile Cys Gly Val Ile Phe Asp Trp Asp Glu Tyr Ser Leu
    50                  55                  60

Asp Leu Cys Ser Asp Ile Asn Gln Leu Asn Glu Tyr Leu Pro Leu Tyr
65                  70                  75                  80

Ala Phe Ile Asn Thr His Ser Thr Met Asp Val Ser Val Gln Asp Met
                85                  90                  95

Arg Met Ala Leu Trp Phe Phe Glu Tyr Ala Leu Gly Gln Ala Glu Asp
            100                 105                 110

Ile Ala Ile Arg Met Arg Gln Tyr Thr Asp Glu Tyr Leu Asp Asn Ile
        115                 120                 125

Thr Pro Pro Phe Thr Lys Ala Leu Phe Thr Tyr Val Lys Glu Arg Lys
    130                 135                 140

Tyr Thr Phe Cys Thr Pro Gly His Met Gly Gly Thr Ala Tyr Gln Lys
145                 150                 155                 160

Ser Pro Val Gly Cys Leu Phe Tyr Asp Phe Phe Gly Gly Asn Thr Leu
                165                 170                 175

Lys Ala Asp Val Ser Ile Ser Val Thr Glu Leu Gly Ser Leu Leu Asp
            180                 185                 190

His Thr Gly Pro His Leu Glu Ala Glu Glu Tyr Ile Ala Arg Thr Phe
        195                 200                 205

Gly Ala Glu Gln Ser Tyr Ile Val Thr Asn Gly Thr Ser Thr Ser Asn
    210                 215                 220

Lys Ile Val Gly Met Tyr Ala Ala Pro Ser Gly Ser Thr Leu Leu Ile
225                 230                 235                 240

Asp Arg Asn Cys His Lys Ser Leu Ala His Leu Leu Met Met Asn Asp
                245                 250                 255

Val Val Pro Val Trp Leu Lys Pro Thr Arg Asn Ala Leu Gly Ile Leu
            260                 265                 270

Gly Gly Ile Pro Arg Arg Glu Phe Thr Arg Asp Ser Ile Glu Glu Lys
        275                 280                 285

Val Ala Ala Thr Thr Gln Ala Gln Trp Pro Val His Ala Val Ile Thr
    290                 295                 300
```

-continued

```
Asn Ser Thr Tyr Asp Gly Leu Leu Tyr Asn Thr Asp Trp Ile Lys Gln
305                 310                 315                 320

Thr Leu Asp Val Pro Ser Ile His Phe Asp Ser Ala Trp Val Pro Tyr
            325                 330                 335

Thr His Phe His Pro Ile Tyr Gln Gly Lys Ser Gly Met Ser Gly Glu
            340                 345                 350

Arg Val Ala Gly Lys Val Ile Phe Glu Thr Gln Ser Thr His Lys Met
            355                 360                 365

Leu Ala Ala Leu Ser Gln Ala Ser Leu Ile His Ile Lys Gly Glu Tyr
            370                 375                 380

Asp Glu Glu Ala Phe Asn Glu Ala Phe Met Met His Thr Thr Thr Ser
385                 390                 395                 400

Pro Ser Tyr Pro Ile Val Ala Ser Val Glu Thr Ala Ala Ala Met Leu
            405                 410                 415

Arg Gly Asn Pro Gly Lys Arg Leu Ile Asn Arg Ser Val Glu Arg Ala
            420                 425                 430

Leu His Phe Arg Lys Glu Val Gln Arg Leu Arg Glu Glu Ser Asp Gly
            435                 440                 445

Trp Phe Phe Asp Ile Trp Gln Pro Pro Gln Val Asp Glu Ala Glu Cys
            450                 455                 460

Trp Pro Val Ala Pro Gly Glu Gln Trp His Gly Phe Asn Asp Ala Asp
465                 470                 475                 480

Ala Asp His Met Phe Leu Asp Pro Val Lys Val Thr Ile Leu Thr Pro
            485                 490                 495

Gly Met Asp Glu Gln Gly Asn Met Ser Glu Glu Gly Ile Pro Ala Ala
            500                 505                 510

Leu Val Ala Lys Phe Leu Asp Glu Arg Gly Ile Val Val Glu Lys Thr
            515                 520                 525

Gly Pro Tyr Asn Leu Leu Phe Leu Phe Ser Ile Gly Ile Asp Lys Thr
            530                 535                 540

Lys Ala Met Gly Leu Leu Arg Gly Leu Thr Glu Phe Lys Arg Ser Tyr
545                 550                 555                 560

Asp Leu Asn Leu Arg Ile Lys Asn Met Leu Pro Asp Leu Tyr Ala Glu
            565                 570                 575

Asp Pro Asp Phe Tyr Arg Asn Met Arg Ile Gln Asp Leu Ala Gln Gly
            580                 585                 590

Ile His Lys Leu Ile Arg Lys His Asp Leu Pro Gly Leu Met Leu Arg
            595                 600                 605

Ala Phe Asp Thr Leu Pro Glu Met Ile Met Thr Pro His Gln Ala Trp
            610                 615                 620

Gln Arg Gln Ile Lys Gly Glu Val Glu Thr Ile Ala Leu Glu Gln Leu
625                 630                 635                 640

Val Gly Arg Val Ser Ala Asn Met Ile Leu Pro Tyr Pro Pro Gly Val
            645                 650                 655

Pro Leu Leu Met Pro Gly Glu Met Leu Thr Lys Glu Ser Arg Thr Val
            660                 665                 670

Leu Asp Phe Leu Leu Met Leu Cys Ser Val Gly Gln His Tyr Pro Gly
            675                 680                 685

Phe Glu Thr Asp Ile His Gly Ala Lys Gln Asp Glu Asp Gly Val Tyr
            690                 695                 700

Arg Val Arg Val Leu Lys Met Ala Gly
705                 710
```

```
<210> SEQ ID NO 9
<211> LENGTH: 54
<212> TYPE: DNA
<213> ORGANISM: Artificial Sequence
<220> FEATURE:
<223> OTHER INFORMATION: 5'-primer for cadA

<400> SEQUENCE: 9
tttgctttct tctttcaata ccttaacggt atagcgtgaa gcctgctttt ttat         54

<210> SEQ ID NO 10
<211> LENGTH: 54
<212> TYPE: DNA
<213> ORGANISM: Artificial Sequence
<220> FEATURE:
<223> OTHER INFORMATION: 3'-primer for cadA

<400> SEQUENCE: 10
agatatgact atgaacgtta ttgcaatatt gaatcacgct caagttagta taaa         54

<210> SEQ ID NO 11
<211> LENGTH: 54
<212> TYPE: DNA
<213> ORGANISM: Artificial Sequence
<220> FEATURE:
<223> OTHER INFORMATION: 5'-primer for ldc

<400> SEQUENCE: 11
ggaggaacac atgaacatca ttgccattat gggacctgaa gcctgctttt ttat         54

<210> SEQ ID NO 12
<211> LENGTH: 53
<212> TYPE: DNA
<213> ORGANISM: Artificial Sequence
<220> FEATURE:
<223> OTHER INFORMATION: 3'-primer for ldc

<400> SEQUENCE: 12
cgccattttt aggactcgta cgcggtaaac gccgtccgtc aagttagtat aaa          53
```